US007002006B2

(12) United States Patent
Song et al.

(10) Patent No.: US 7,002,006 B2
(45) Date of Patent: Feb. 21, 2006

(54) PROTECTION OF NUCLEOSIDES

(75) Inventors: Quanlai Song, Encinitas, CA (US); Bruce S. Ross, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 201 days.

(21) Appl. No.: 10/365,183

(22) Filed: Feb. 12, 2003

(65) Prior Publication Data

US 2004/0158055 A1 Aug. 12, 2004

(51) Int. Cl.
*C07H 19/00* (2006.01)
(52) U.S. Cl. .................. 536/28.1; 536/22.1; 536/27.11
(58) Field of Classification Search ............... 536/27.1, 536/28.1, 22.1, 27.11
See application file for complete search history.

(56) References Cited

U.S. PATENT DOCUMENTS

| | | | |
|---|---|---|---|
| 3,687,808 A | 8/1972 | Merigan et al. .......... 195/28 N |
| 4,415,732 A | 11/1983 | Caruthers et al. ............. 536/27 |
| 4,458,066 A | 7/1984 | Caruthers et al. ............. 536/27 |
| 4,469,863 A | 9/1984 | Ts'o et al. ..................... 536/27 |
| 4,500,707 A | 2/1985 | Caruthers et al. ............. 536/27 |
| 4,668,777 A | 5/1987 | Caruthers et al. ............. 536/27 |
| 4,725,677 A | 2/1988 | Köster et al. .................. 536/27 |
| 4,845,205 A | 7/1989 | Huynh Dinh et al. ........ 536/28 |
| 4,973,679 A | 11/1990 | Caruthers et al. ............. 536/27 |
| 5,034,506 A | 7/1991 | Summerton et al. ........ 528/391 |
| 5,118,800 A | 6/1992 | Smith et al. ................... 536/23 |
| 5,124,047 A | 6/1992 | Quach et al. ................ 210/699 |
| 5,130,302 A | 7/1992 | Spielvogel et al. ........... 514/45 |
| 5,134,066 A | 7/1992 | Rogers et al. ................. 435/91 |
| 5,138,045 A | 8/1992 | Cook et al. .................... 536/27 |
| RE34,069 E | 9/1992 | Köster et al. .................. 536/27 |
| 5,166,315 A | 11/1992 | Summerton et al. ....... 528/406 |
| 5,175,273 A | 12/1992 | Bischofberger et al. ...... 536/27 |
| 5,185,444 A | 2/1993 | Summerton et al. .......... 544/81 |
| 5,212,295 A | 5/1993 | Cook ......................... 536/26.7 |
| 5,214,134 A | 5/1993 | Weis et al. ................. 536/25.3 |
| 5,216,141 A | 6/1993 | Benner .................... 536/27.13 |
| 5,218,105 A | 6/1993 | Cook et al. ............... 536/25.31 |
| 5,223,168 A | 6/1993 | Holt ............................ 252/142 |
| 5,235,033 A | 8/1993 | Summerton et al. ........ 528/391 |
| 5,264,562 A | 11/1993 | Matteucci .................. 536/23.1 |
| 5,264,564 A | 11/1993 | Matteucci .................. 536/23.1 |
| 5,278,302 A | 1/1994 | Caruthers et al. .......... 536/24.5 |
| 5,321,131 A | 6/1994 | Agrawal et al. ......... 536/25.34 |
| 5,359,044 A | 10/1994 | Cook et al. ................ 536/23.1 |
| 5,367,066 A | 11/1994 | Urdea et al. ............... 536/24.3 |
| 5,378,825 A | 1/1995 | Cook et al. ............... 536/25.34 |
| 5,393,878 A | 2/1995 | Leumann .................. 536/28.2 |
| 5,405,938 A | 4/1995 | Summerton et al. ........ 528/406 |
| 5,432,272 A | 7/1995 | Benner ...................... 536/25.3 |
| 5,434,257 A | 7/1995 | Matteucci et al. ......... 536/24.3 |
| 5,446,137 A | 8/1995 | Maag et al. ................ 536/23.1 |
| 5,455,233 A | 10/1995 | Spielvogel et al. ............ 514/44 |
| 5,457,187 A | 10/1995 | Gmeiner et al. ........... 536/25.5 |
| 5,459,255 A | 10/1995 | Cook et al. ............... 536/27.13 |
| 5,466,677 A | 11/1995 | Baxter et al. .................. 514/44 |
| 5,466,786 A | 11/1995 | Buhr et al. ............... 536/26.26 |
| 5,470,967 A | 11/1995 | Huie et al. ................. 536/24.3 |
| 5,484,908 A | 1/1996 | Froehler et al. .......... 536/24.31 |
| 5,489,677 A | 2/1996 | Sanghvi et al. ............ 536/22.1 |
| 5,502,177 A | 3/1996 | Matteucci et al. |
| 5,506,351 A | 4/1996 | McGee ...................... 536/55.3 |
| 5,514,785 A | 5/1996 | Van Ness et al. .......... 536/22.1 |
| 5,519,126 A | 5/1996 | Hecht ........................ 536/24.3 |
| 5,519,134 A | 5/1996 | Acevedo et al. ............. 544/243 |
| 5,521,302 A | 5/1996 | Cook ....................... 536/25.31 |
| 5,525,711 A | 6/1996 | Hawkins et al. ........... 536/22.1 |
| 5,539,082 A | 7/1996 | Nielsen et al. .............. 530/300 |
| 5,541,307 A | 7/1996 | Cook et al. ................ 536/23.1 |
| 5,552,540 A | 9/1996 | Haralambidis ........... 536/25.34 |
| 5,554,746 A | 9/1996 | Ravikumar et al. ......... 540/200 |
| 5,561,225 A | 10/1996 | Maddry et al. ............. 536/23.1 |
| 5,567,811 A | 10/1996 | Misiura et al. ........... 536/25.34 |
| 5,571,902 A | 11/1996 | Ravikumar et al. ........ 536/22.1 |
| 5,576,427 A | 11/1996 | Cook et al. ................ 536/23.1 |
| 5,578,718 A | 11/1996 | Cook et al. .............. 536/27.21 |
| 5,587,361 A | 12/1996 | Cook et al. .................... 514/44 |

(Continued)

FOREIGN PATENT DOCUMENTS

EP 216860 4/1987

(Continued)

OTHER PUBLICATIONS

Altmann, K. et al., "Second-Generation Antisense Oligonucleotides: Structure-Activity Relationships and the Design of Improved Signal-Transduction Inhibitors," *Biochem. Soc. Trans.*, 1996, 24, 630-637.

(Continued)

*Primary Examiner*—James O. Wilson
*Assistant Examiner*—Howard V. Owens, Jr.
(74) *Attorney, Agent, or Firm*—ISIS Patent Department; Woodcock Washburn LLP

(57) ABSTRACT

A process of manufacturing protected nucleosides comprises reacting a nucleoside with a protecting reagent in the presence of a regioselective activator to produce a regioselectively protected nucleoside. In some embodiments of the inventive method, an optionally substituted trityl or optionally substituted pixyl group is selectively added to the 5'-O-position of a nucleoside in the presence of lutidine as activator or activator/solvent. The inventive method results in improved selectivity of the 5'-O-position over the 3'-O-position, thereby improving overall product yield and purity, and permitting simplified purification protocols, in some cases obviating the need for chromatography to produce a purified protected nucleoside suitable for automated synthesis of oligonucleotides, such as primers, probes and antisense molecules.

62 Claims, No Drawings

U.S. PATENT DOCUMENTS

| | | | |
|---|---|---|---|
| 5,587,469 A | 12/1996 | Cook et al. | 536/23.1 |
| 5,587,470 A | 12/1996 | Cook et al. | 536/23.1 |
| 5,591,722 A | 1/1997 | Montgomery et al. | 514/45 |
| 5,594,121 A | 1/1997 | Froehler et al. | 536/23.5 |
| 5,596,086 A | 1/1997 | Matteucci et al. | 536/22.1 |
| 5,596,091 A | 1/1997 | Switzer | 536/24.5 |
| 5,597,909 A | 1/1997 | Urdea et al. | 536/24.3 |
| 5,599,797 A | 2/1997 | Cook et al. | 514/44 |
| 5,602,240 A | 2/1997 | De Mesmaeker et al. | 536/23.1 |
| 5,608,046 A | 3/1997 | Cook et al. | 536/23.1 |
| 5,610,289 A | 3/1997 | Cook et al. | 536/25.34 |
| 5,610,300 A | 3/1997 | Altmann et al. | 544/244 |
| 5,614,617 A | 3/1997 | Cook et al. | 536/23.1 |
| 5,618,704 A | 4/1997 | Sanghvi et al. | 435/91.5 |
| 5,623,070 A | 4/1997 | Cook et al. | 536/27.6 |
| 5,627,053 A | 5/1997 | Usman et al. | 435/91.1 |
| 5,633,360 A | 5/1997 | Bischofberger et al. | 536/22.1 |
| 5,639,867 A * | 6/1997 | Brill | 536/22.1 |
| 5,639,873 A | 6/1997 | Barascut et al. | 536/25.3 |
| 5,645,985 A | 7/1997 | Froehler et al. | 435/6 |
| 5,646,265 A | 7/1997 | McGee | 536/25.34 |
| 5,646,269 A | 7/1997 | Matteucci et al. | 536/26.7 |
| 5,658,873 A | 8/1997 | Bertsch-Frank et al. | 510/375 |
| 5,663,312 A | 9/1997 | Chaturvedula | 536/22.1 |
| 5,670,633 A | 9/1997 | Cook et al. | 536/23.1 |
| 5,677,437 A | 10/1997 | Teng et al. | 536/23.1 |
| 5,681,941 A | 10/1997 | Cook et al. | 536/23.1 |
| 5,700,920 A | 12/1997 | Altmann et al. | 536/221 |
| 5,750,692 A | 5/1998 | Cook et al. | 544/253 |
| 5,763,588 A | 6/1998 | Matteucci et al. | 536/22.1 |
| 5,792,608 A | 8/1998 | Swaminathan et al. | 435/6 |
| 5,817,781 A | 10/1998 | Swaminathan et al. | 536/22.1 |
| 5,830,653 A | 11/1998 | Froehler et al. | 435/6 |
| 5,859,221 A | 1/1999 | Cook et al. | 536/23.1 |
| 6,005,096 A | 12/1999 | Matteucci et al. | 536/26.6 |
| 6,147,200 A | 11/2000 | Manoharan et al. | 536/23.1 |
| 6,172,209 B1 | 1/2001 | Manoharan et al. | 536/23.1 |
| 6,242,591 B1 | 6/2001 | Cole et al. | 536/25.3 |
| 6,262,241 B1 | 7/2001 | Cook et al. | 536/22.1 |
| 6,271,358 B1 | 8/2001 | Manoharan et al. | 536/23.1 |
| 6,576,752 B1 | 6/2003 | Manoharan et al. | 536/23.2 |
| 2002/0150936 A1 * | 10/2002 | Beigelman et al. | 435/6 |

FOREIGN PATENT DOCUMENTS

| | | |
|---|---|---|
| WO | WO 89/12060 | 12/1989 |
| WO | WO 90/02749 | 3/1990 |
| WO | WO 90/15065 | 12/1990 |
| WO | WO 91/15500 | 10/1991 |
| WO | WO 91/18997 | 12/1991 |
| WO | WO 92/05186 | 4/1992 |
| WO | WO 92/19637 | 11/1992 |
| WO | WO 92/20822 | 11/1992 |
| WO | WO 92/20823 | 11/1992 |

OTHER PUBLICATIONS

Altmann, K.-H. et al., "Second Generation of Antisense Oligonucleotides: From Nuclease Resistance to Biological Efficacy in Animals," *Chimia*, 1996, 50, 168-176.

Altmann, K. et al., "Second Generation Antisense Oligonucleotides-Inhibition of Pkc-1 And c-RAF Kinase Expression by Chimeric Oligonucleotides Incorporating 6-Substituted Carbocyclic Nucleosides and 2'-O-Ethylene Glycol Substituted Ribonucleosides," *Nucleosides & Nucleotides*, 1997, 16(7-9), 917-926.

Alul, R. H. et al., "Oxalyl-CPG: a labile support for synthesis of sensitive oligonucleotide derivatives," *Nucl. Acid Res.*, 1991, 19, 1527-1532.

Atherton, E. et al., "The Polyamide Method of Solid Phase Peptide and Oligonucleotide Synthesis," *Bioorganic Chemistry 8*, 1979, 351-370.

Atherton, E. et al., "Polyamide Supports for Polypeptide Synthesis," *J. Am. Chem. Soc.*, 1975, 97, 6584-6585.

Baker, B. F. et al., "2-O-(2-Methoxy)ethyl-modified Anti-intercellular Adhesion Molecule 1 (ICAM-1) Oligonucleotides Selectively Increase the ICAM-1 Translation Initiation Complex in Human Umbilical Vein Endothelial Cells," *J.Biol. Chem.*, 1997, 272, 11994-12000.

Bayer, E. et al., "A New Support for Polypeptide Synthesis in Columns," *Tetrahedron Letters*, 1970, No. 51, 4503-4505.

Beaucage, S. L. et al., "Oligodeoxyribonucleotides Synthesis," *Methods in Molecular Biology*, 1993, vol. 20, Chap. 3, Agrawal, S., ed., Humana Press Inc., Totowa, NJ, 33-61.

Berg, R. H. et al., "Long-Chain Polystyrene-Grafted Film Matrix: A New Support for Solid-Phase Peptide Synthesis[1]," *J. Am. Chem. Soc.*, 1989, 111, 8024-8026.

Bonora, G.M., et al., "A liquid-phase process suitable for large-scale synthesis of phosphorothioate oligonucleotides," *Organic Process Res. & Develop.*, 2000, 4, 225-231.

Conte, M. R. et al., "Confirmational Properties and Thermodynamics of the RNA Duplex r(CGCAAAUUUGCG)2: Comparison with the DNA Analogue d(CGCAAATTTGCG)2," *Nucl. Acids Res.*, 1997, 25(13), 2627-2634.

Coull, J. M. et al., "Synthesis and Characterization of a Carbamate-Linked Oligonucleoside," *Tetrahedron Letts.*, 1987, 28, 745-748.

Crooke, S. T. , "Progress in Antisense Therapeutics," *Medicinal Research Reviews*, 1996, 16(4), 319-344.

Damha, M. J. et al., "Duplex Recognition by Oligonucleotides Containing 2'-Deoxy-2'-fluoro-D-arabinose and 2'-Deoxy-2'-fluoro-D-ribose. Intermolecular 2'-OH—Phosphate Contacts versus Sugar Puckering in the Stabilization of Triple-Helical Complexes," *Bioconjugate Chem.*, 1999, 10, 299-305.

Damha, M. J. et al., "Hybrids of RNA and Arabinonucleic Acids (ANA and 2'F-ANA) Are Substrates of Ribonuclease H," *J.Am. Chem.Soc.*, 1998, 120, 12976-12977.

Daniels, S. B. et al., "Membranes as Solid Supports for Peptide Synthesis," *Tetrahedron Letters*, 1989, 30 (33), 4345-4348.

DeMesmaeker, A., et al., "Antisense oligonucleotides," *Acc. Chem. Res.*, 1995, 28, 366-374.

Eckstein, F. (Ed.), Oligonucleotides and Analogues, a Pratical Approach, Oxford University Press, New York, 1991, 57 and 256-259.

Egli, M. et al., "RNA Hydration: A Detailed Look," *Biochemistry*, 1996, 35, 8489-8494.

Eichler, J. et al., "Application of Cellulose Paper as Support Material in Simultaneous Solid Phase Peptide Synthesis," *Collect. Czech. Chem. Commun.*, 1989, 54, 1746-1752.

Englisch, U. et al., "Chemically Modified Oligonucleotides as Probes and Inhibitors," *Angew. Chem. Int. Ed. Eng.*, 1991, 30, 613-629.

Federoff, O. Y. et al., "Structure of a DNA: RNA Hybrid Duplex Why Rnase H Does Not Cleave Pure RNA," *J. Mol. Biol.*, 1993, 233, 509-523.

Flanagan, W. M. et al., "A cytosine analog that confers enhanced potency to antisense oligonucleotides," *Proc. Natl. Acad. Sci. USA*, Mar. 1999, 96, 3513-3518.

Freier, S. M. et al., "The ups and downs of nucleic acid duplex stability: structureBstability studies on chemically-modified DNA:RNA duplexes," *Nucleic Acids Research*, 1997, 25(22), 4429-4443, XP-002132784.

Froehler, in Methods in Molecular Biology: Protocols for Oligonucleotides and Analogs, Agrawal (Ed.), *Humana press, Totowa*, 1993, 20, 63-80.

Geysen, H. M. et al., "Use of peptide synthesis of probe viral antigens for epitopes to a resolution of a single amino acid," *Proc. Natl. Acad. Sci. USA*, 1984, 81, 3998-4002.

Gonzalez, C. et al., "Structure and Dynamics of a DNA-RNA Hybrid Duplex with a Chral Phosphorothioate Moiety: NMR and Molecular Dynamics with Conventional and Time-Averaged Restraints," *Biochemistry*, 1995, 34, 4969-4982.

Gorman, J. J., "An Apparatus for Simultaneous Manual Solid-Phase Synthesis of Multiple Peptide Analogs,"*Analyt. Biochem.*, 1984, 136, 397-406.

Gravert, D., et al., "Organic synthesis on soluble polymer supports: liquid-phase methodologies," *Chem . Rev.*, 1997, 97, 489-509.

Hewitt, J. M. et al., "Structural Determination of Silicon-Containing Oligonucleotides by $^1H$-$^{29}Si$ Long-Range Heteronuclear Multiple Quantum Correlation NMR Spectroscopy," 1992, 11, 1661-1666.

Holm, et al., in Proceedings of the $20^{th}$ European Peptide Symposium, Jung, G., et al. (Eds.), *Walter de Gruyter& Co., Berlin*, 1989, 208-210.

Horton, N. C. et al., "The Structure of an RNA/DNA Hybrid: A Substrate of the Ribonuclease Activity of HIV-1 Reverse Transcriptase," *J. Mol. Biol.*, 1996, 264, 521-533.

Houghten, R. A., "General method for the rapid solid-phase synthesis of large numbers of peptides: Specifically of antigen-antibody interaction at the level of individual amino acids," *Proc. Natl. Acad. Sci. USA*, 1985, 82, 5131-5135.

Kent, S. B. et al., "Preparation and Properties of tert-Butlyoxycarbonylaminoacyl-4-(oxymethyl) phenylacetamidomethyl-(Kel F-g-Styrene) Resin, an Insoluble, Noncrossedlinked Support for Solid Phase Peptide Synthesis," *Israel J. Chem.*, 1978, 17, 243-247.

Krchnak, V. et al., "Multiple continuous-flow solid-phase peptide synthesis," *Int. J. Peptide Protein Res.*, 1989, 33, 209-213.

Kroschwitz, J.I. (Ed.), The Concise Encyclopedia of Polymer Science and Engineering, *John Wiley & Sons*, 1990, 858-859.

Kurchavov, N.A., et al., "A new phosphoramidite reagent for the incorporation of diazaphenoxazinone nucleoside with enhanced base-pairing properties into oligodeoxynucleotides," *Nucleosides and Nucleotides*, 1997, 16, 1837-1846.

Lane, A. N. et al., "NMR Assignments and Solution Conformation of the DNA-RNA Hybrid Duplex d (GTGAACTT)-r(AAGUUCAC)," *Eur. J. Biochem.*, 1993, 215, 297-306.

Lebl, M., et al., "Simulation of continuous solid phase synthesis: synthesis of methionine enkephalin and its analogs," *Peptide Res.*, 1989, 2(4), 297-300.

Lesnik, E. A. et al., "Relative Thermodynamic Stability of DNA, RNA, and DNA: RNA Hybrid Duplexes: Relationship with Base Composition and Structure," *Biochemistry*, 1995, 34(34), 10807-10815.

Lin, K.-Y. et al., "Tricyclic 2'-Deoxycytidine Analogs: Synthesis and Incorporation into Oligodeoxynucleotides Which Have Enhanced Binding to Complementary RNA," *J. Am. Chem. Soc.*, 1995, 117, 3873-3874.

Lin, K.-Y. et al., "A Cytosine Analogue Capable of Clamp-Like Binding to a Guanine in Helical Nucleic Acids,"*J. Am. Chem. Soc.*, 1998, 120(33), 8531-8532.

Martin, von P., "Ein neuer Zugang zu 2'-O-Alkylribonucleosiden und Eigenschaften deren Oligonucleotide," *Helvetica Chemica Acta*, 1995, 78, 486-504.

Mertes, M.P., et al., "Synthesis of carbonate analoges of dinucleosides. 3'-thymidinyl 5'-thymidiny carbonate ,3'-thymidinyl 5'-(5-fluoro-2'deoxyuridinyl) carbonate, and 3'-(5'-fluoro-2'-deoxyuridinyl) 5'thymidinyl carbonate," *J. Med. Chem.*, Jan. 1969, 12, 154-157.

Mungall, W. S. et al., "Carbamate Analogues of Oligonucleotides," *J. Org. Chem.*, 1977, 42, 703-706.

Musichi, B., et al., "Synthesis of carbohydrate sulfonates and sulfonate esters," *J. Org. Chem.*, 1990, 55, 4231-4233.

Parr, W. et al., "Solid-Phase Peptide Synthesis on an Inorganic Matrix having Organic Groups on the Surface," *Angew Chem. Internat. Edit*, 1972, 11 (4), 314-315.

Atherton, E., et al., "Peptide synthesis. Part 2. Procedures for solid-phase synthesis using $N^{\alpha}$-fluorenylmethoxycarbonylamino-acids on polyamide supports. Synthesis of substance P and of acyl carrier protein 65-74 decapeptide," *J.C.S. Perkins I*, 1981, 538-546.

Reese, C. B. et al., "The Chemical Synthesis of Oligo-and Poly-Nucleotides by the Phosphotriester Approach," *Tetrahedron*, 1978, 34, 3143-3179.

Rennenberg, D., et al., "Antisense properties of tricycle-DNA," *Nucleic Acids Res.*, 2002, 30(13), 2751-2757.

Reynolds, R. C. et al., "Synthesis of Thymidine Dimers Containing Internucleoside Sulfonate and Sulfonamide Linkages," *J. Org. Chem.*, 1992, 57, 2983-2985.

Sanghvi, Y.S., "Heterocyclic base modifications in nucleic acids and their applications in antisense oligonucleotides," Antisense Research and Applications, *CRC Press*, 1993, Crooke, S.T., et al. (Eds.), Chapter 15, 273-288.

Scott, R.P.W. et al., "The Use of Resin Coated Glass Beads in the Form of a Packed Bed for the Solid Phase Synthesis of Peptides," *J. Chromatographic Science*,Oct. 1971, 9, 577-590.

Searle, M. S. et al., "On the Stability of Nucleic Acid Structures in Solution: Enthalpy-Entropy Compensations, Internal Rotations and Reversibility," *Nucl. Acids Res.*, 1993, 21(9), 2051-2056.

Sood, A. et al., "Boron-Containing Nucleic Acids. 2. Synthesis of Oligodeoxynucleoside Boranophosphates," *J. Am. Chem. Soc.*, 1990, 112, 9000-9001.

Stirchak, E. P. et al., "Uncharged Stereoregular Nucleic Acid Analogs. I. Synthesis of a Cytosine-Containing Oligomer with Carbamate Internucleoside Linkages," *J. Org Chem.*, 1987, 52(19), 4202-4206.

Stirchak, E. P. et al., "Uncharged stereoregular nucleic acid analogs: 2. Morpholino nucleoside oligomer with carbamate internucleoside linkages," *Nucl. Acids Res.*, 1989, 17, 6129-6134.

Tregear, G. W., "Graft Copolymers as Insoluble Supports in Peptide Synthesis," *Chemistry and Biology of Peptides*, 1972, 175-178.

Wang, H. et al., "Solid Phase Synthesis of Neutral Oligonucleotide Analogues," *Tetrahedron Letts.*, 1991, 32, 7385-7388.

Vester, et al., "LNAzymes: incorporation of LNA-type monomers into DNAzymes markedly increases RNA cleavage," *J. Am. Chem. Soc.*, 2002, 124, 13682-13683.

Wang, H., et al., "Solid phase synthesis of neutral oligonucleotide analogues," *Tet. Lett.*, 1991, 32(50), 7385-7388.

Wang, J., et al., "Synthesis and binding property of an oligonucleotide containing tetrafluorophenoxazine," *Tetrahedron Lett.*, 1998, 39, 8385-8388.

Wright, P. et al., "Large Scale Synthesis of Oligonucleotides via phosphoramidite Nucleosides and a High-loaded Polystyrene Support," *Tetrahedron Letts.*, 1993, 34(21), 3373-3376.

U.S. Appl. No. 09/349,040, filed Jul. 7, 1999, Manoharan et al.

U.S. Appl. No. 09/370,541, filed Aug. 9, 1999, Manoharan et al.

U.S. Appl. No. 10/013,295, filed Dec. 10, 2001, Manoharan et al.

U.S. Appl. No. 10/155,920, filed May 24, 2002, Manoharan et al.

Taj, S.A.S., et al., "Process development for the synthesis of 5'-0-(2-methoxyethyl)-guanosine—a potential precursor for the second generation antisense oligonucleotides: an improved process for the preparation of 2'-0-alkyl-2,6-diaminopurine riboside," *Nucleosides, Nucleotides & Nucleic Acids*, 2003, 1327-1330.

* cited by examiner

PROTECTION OF NUCLEOSIDES

FIELD OF THE INVENTION

The present invention is directed to the field of nucleoside protection. More particularly, the present invention relates to the protection of a nucleoside using a hindered aryl base as an activator.

BACKGROUND OF THE INVENTION

Antisense compounds have shown great promise as therapeutics, diagnostics and aids to therapeutic target validation. An antisense compound modulates a protein's activity by attenuating the concentration of polynucleotides, especially RNA, involved in protein synthesis. This is in contrast to conventional therapeutic methods, which seek to modulate protein activities by direct interaction between putative drugs and proteins. The effect of an antisense compound's interaction with intracellular polynucleotides is thus a predictable, albeit indirect, modulation of the activity of the protein or peptide that the cell normally manufactures using the polynucleotide as a template.

In general, antisense methods involve determining the sequence of a coding polynucleotide (e.g. mRNA) that encodes for a certain protein, developing a relatively short oligomer (antisense compound) that selectively binds to the polynucleotide (sense strand), and introducing the oligomer into the intracellular environment. Antisense methods can predictably modulate gene expression through a variety of mechanisms. In one such mechanism, the antisense strand blocks translation by competitively binding to the sense strand. In another mechanism, an antisense strand containing a stretch of DNA (e.g. phosphorothioate DNA) binds to the sense strand, and then the DNA-RNA hybrid is recognized by RNAse H, an endonuclease, which selectively cleaves the DNA-RNA hybrid, thereby reducing intracellular RNA levels. Another methodology involves the interaction between small double stranded RNA oligomers and mRNA. In such mechanisms, interaction between the RISC complex, the antisense strand of the small double-stranded RNA and intracellular mRNA results in cleavage and degradation of the mRNA.

As antisense molecules have become accepted as therapeutic and diagnostic agents, the need to produce oligonucleotides in large quantities has increased as well. The most commonly used antisense compounds to date have been oligonucleotides, phosphorothioate oligonucleotides and second generation oligonucleotides having one or more modified ribosyl sugar units, and more recently, ribosyl sugar units. The methods for making these three types of antisense oligomers are roughly similar, and include the phosphotriester method, as described by Reese, *Tetrahedron* 1978, 34, 3143; the phosphoramidite method, as described by Beaucage, in *Methods in Molecular Biology: Protocols for Oligonucleotides and Analogs*; Agrawal, ed.; Humana Press: Totowa, 1993, Vol. 20, 33–61; and the H-phosphonate method, as described by Froehler in *Methods in Molecular Biology: Protocols for Oligonucleotides and Analogs* Agrawal, ed.; Humana Press: Totowa, 1993, Vol. 20, 63–80. Of these three methods, the phosphoramidite method has become a defacto standard in the industry.

A typical oligonucleotide synthesis using phosphoramidite chemistry (i.e. the amidite methodology) is set forth below. First, a primer support is provided in a standard synthesizer column. The primer support is typically a solid support (supt) having a linker (link) covalently bonded thereto. It is common to purchase the primer support with a first 5'-protected nucleoside bonded thereto.

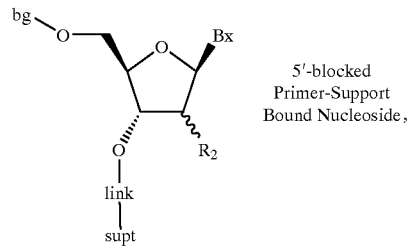

5'-blocked Primer-Support Bound Nucleoside,

Primer support: bg is a 5'-blocking group, Bx is a nucleobase, $R_{2'}$ is H, OH, OH protected with a removable protecting group, or a 2'-substituent, such as 2'-deoxy-2'-methoxyethoxy (2'-O-MOE), and link is the covalent linking group, such as a succinyl group, which joins the nucleoside to the support, supt.

(A) The 5'-blocking group bg (e.g. 4,4'-dimethoxytrityl) is first removed (e.g. by exposing the 5'-blocked primer-support bound nucleoside to an acid), thereby producing a support-bound nucleoside of the formula:

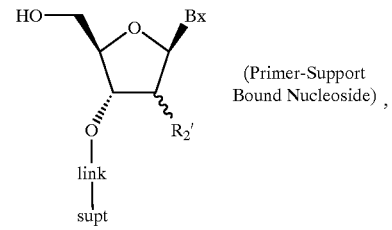

(Primer-Support Bound Nucleoside),

Activated primer support: wherein supt is the solid support, link is the linking group, Bx is a nucleobase, $R_{2'}$ is H, OH, OH protected with a removable protecting group, or a 2'-substituent.

(B) The column is then washed with acetonitrile, which acts to both "push" the regent (acid) onto the column, and to wash unreacted reagent and the removed 5'-blocking group (e.g. trityl alcohol) from the column.

(C) The primer support is then reacted with a phosphitylation reagent (amidite), which is dissolved in acetonitrile, the amidite having the formula:

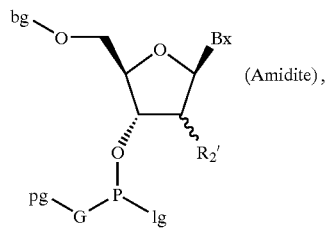

(Amidite), wherein bg is a 5'-blocking group, 1 g is a leaving group, G is O or S, pg is a phosphorus protecting group, and $R_{2'}$ and Bx have, independent of the analogous variables on the primer support, the same definitions as previously defined.

The product of this reaction is the support-bound phosphite dimer:

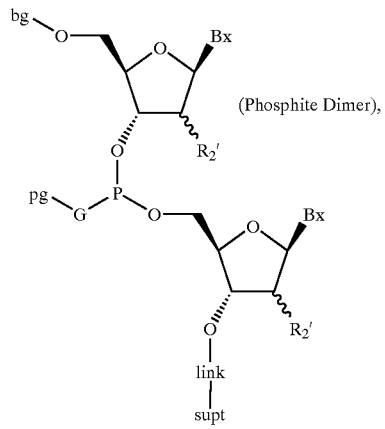

(Phosphite Dimer),

Support-bound wherein each of the variables bg, pg, G, $R_{2'}$ and Bx is independently defined above, link is the linker and supt is the support, as defined above.

(D) The support-bound dimer is then typically washed with acetonitrile.

(E) A capping reagent in acetonitrile is then added to the column, thereby capping unreacted nucleoside.

(F) The column is then washed again with acetonitrile.

(G) The support-bound dimer is then typically reacted with an oxidizing agent, such as a thiolating agent (e.g. phenylacetyl disulfide), in acetonitrile, to form a support-bound phosphate triester:

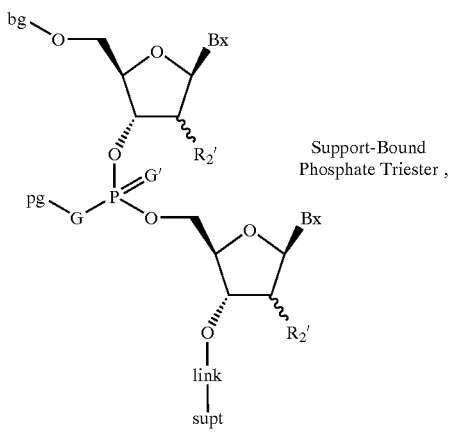

Support-Bound Phosphate Triester, wherein G' is O or S and the other variables are defined herein.

(H) The support-bound phosphate triester is then typically washed with acetonitrile.

Steps (A)–(F) are then repeated, if necessary, a sufficient number of times to prepare a support-bound, blocked oligonucleotide having the formula:

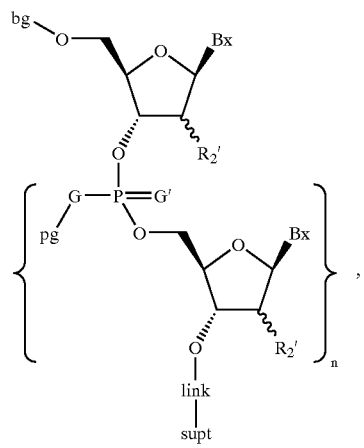

wherein n is a positive integer (typically about 7 to about 79).

The phosphorus protecting groups pg are then typically removed from the oligomer to produce a support-bound oligomer having the formula:

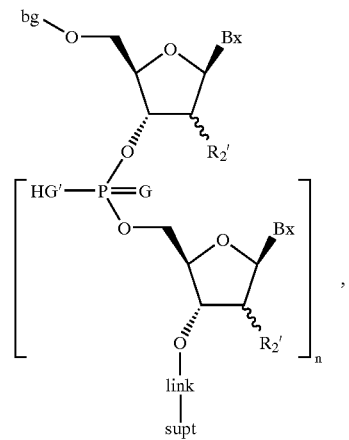

which, after washing with a suitable wash solvent, such as acetonitrile, is typically cleaved from the solid support, purified, 5'-deblocked, and further processed to produce an oligomer of the formula:

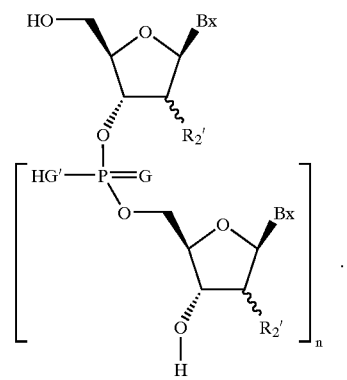

The person having skill in the art will recognize that G'H bound to a P(V) phosphorus is generally is ionized at physiologic pH, and that therefore, wherever G'H appears in the formulae above, or hereafter, G'⁻ is synonymous therewith (the O⁻ or S⁻ being countered by a suitable cation, such as Na⁺).

In the foregoing background, bg is a blocking group, such as an acid-labile group. Such groups include the monomethoxytrityl group (MMT), the dimethoxytrityl group (DMT), the pixyl group, etc. DMT is the most widely used 5'-hydroxylprotection group for nucleoside derivatives used in automated nucleic acid synthesizers. DMT is also known in the literature as 4,4'-dimethoxytriphenylmethyl (and is alternatively abbreviated DMTr). DMT has the advantage of being nearly quantitatively removed with dilute acid during cyclical automated synthesis. The removed DMT is in the form of a cation, which can be detected and measured by an in-line ultraviolet spectrophotometer to indicate the progress of the reaction. During the synthesis of the nucleoside monomers, the DMT group is selective for the 5' primary hydroxyl over the 3' secondary hydroxyl of the nucleoside. Typically, the reaction between the base-protected nucleoside and DMT chloride is carried out in pyridine as a solvent/base with 1.2–1.3 molar equivalents of the DMT chloride. The selectivity for the 5'-OH is not optimal, so initially there is a mixture of 5'-O-mono and 3'-O-mono substituted DMT products. As the reaction completes it is desirable to force the reaction to the point in which the 3' mono DMT is converted to the 3',5' bis DMT product because it is easier to separate. The mono DMT derivatives have very similar physical properties and are difficult to separate. Furthermore, the 3' DMT product will react in the next step, phosphitylation, and will not be separable and thus will be incorporated into the desired oligonucleotide. It will also be difficult to detect once incorporated as the mass of the resulting oligonucleotide is the same. In the process, the 5' mono desired product is also partially converted to the bis product. As a result, the yield of purified 5' mono DMT product is reduced substantially. Typically yields of 70–80% of theory are the best to be expected. This reduction in yield is especially harmful when using more expensive, modified nucleosides such as 2'-O-alkyl-ribonucleosides.

There is a need for a method of regioselectively protecting a nucleoside, especially at the 5'-position of a ribonucleoside or a deoxy ribonucleoside, which provides for yields of protected nucleoside of greater than about 80% of theory. There is especially a need for such a method that provides for yields of greater than about 85% of theory, preferably of greater than about 90% of theory, and more preferably of greater than about 95% of theory.

There is also a need for a method of regioselectively protecting a nucleoside, which provides a nucleoside having excellent purity.

There is also a need for a method of regioselectively protecting a nucleoside, which provides greater regioselectivity than pyridine in the analogous reaction.

There is also a need for a protected nucleoside, especially a 5'-protected nucleoside, which has a minimal degree of 3'-protected impurity. There is especially a need for a 5'-protected nucleoside that has less than about 1%, and more preferably less than about 0.5%, and even more preferably less than about 0.1% of the 3'-protected impurity.

There is also a need for a method that provides a 5'-protected nucleoside that is suitable for preparing phosphoramidites for use in automated synthesis of oligonucleotides, which method excludes a chromatography step.

There is also a need for a method of preparing a 5'-protected phosphoramidite, wherein the phosphoramidite is substantially free of the 3'-protected impurity.

SUMMARY OF THE INVENTION

The foregoing and further needs are met by embodiments of the present invention, which provide a process comprising contacting a nucleoside with a hindered aryl amine activator and a protecting reagent to produce a regioselectively protected nucleoside.

The foregoing and further needs are further met by embodiments of the present invention, which provide steps for purifying a protected nucleoside.

The foregoing and further needs are further met by embodiments of the present invention, which provide steps for derivatizing a protected nucleoside with a reagent selected from a diacid and a diacid anhydride to form an acid-derivatized nucleoside, purifying the acid-derivatized nucleoside, and removing the diacid group to form a purified protected nucleoside.

The foregoing and further needs are further met by embodiments of the present invention, which provide steps for linking the protected nucleoside to a support via the acid-substituent group on the acid-derivatized nucleoside.

Other objects, advantages and improvements to the art provided by the invention will be apparent to the person having skill in the art upon consultation of the following description and claims.

DETAILED DESCRIPTION OF THE INVENTION

The present invention relates to a method of producing protected nucleosides in high yield and excellent purity. In some embodiments of the invention, it provides a method of producing 5'-O-protected nucleosides, wherein the nucleosides are protected with a protecting group orthogonal to other protecting groups used in oligonucleotide synthesis. In more specific embodiments, the invention provides a method of producing protected nucleosides, in which the nucleosides are protected at the 5'-O-position with an acid-labile protecting group. Although a preferred acid-labile protecting group is DMT (4,4'-dimethoxytrityl), other acid-labile protecting groups are contemplated within the scope of the invention. Particularly suitable acid-labile protecting groups include MMT (4-monomethoxytrityl), and other trityl derivatives, as well as the pixyl (9-phenylxanthen-9-yl) group, the thiopixyl (9-phenylthioxanthen-9-yl) and substituted pixyl and thiopixyl groups. While the examples below are directed to DMT as the acid-labile protecting group, the method is applicable to a wider range of acid-labile protecting groups, and especially protecting groups that are believed to be added by SN1-type reactions.

The most widely used 5'-hydroxyl protection group for nucleoside derivatives intended for use in automated nucleic acid synthesizers is the 4,4'-dimethoxytriphenylmethyl (DMT). DMT has the advantage of being nearly quantitatively removed with dilute acid consistent with the commonly used automated synthesis cycles. As the DMT group is removed, it is thought to be present in solution as a cation, which can be sensitively measured by an in-line ultraviolet spectrophotometer to indicate the progress of the reaction. It has been the practice in the art to carry out the reaction between a base-protected nucleoside and DMT chloride in pyridine as a solvent/base with 1.2–1.3 molar equivalents of the DMT chloride to 1.0 equivalents of base-protected nucleoside (hereinafter nucleoside, as not all nucleoside bases need be protected during synthesis). During the synthesis of protected nucleoside monomers, the DMT group is somewhat selective for the 5'-primary hydroxyl over the 3'-secondary hydroxyl of the nucleoside. The selectivity for the 5'-OH is not very high, so initially there is a mixture of 5'-mono and 3'-mono substituted DMT products. As the reaction goes toward completion it is desirable to force the reaction to the point at which the 3' mono DMT is converted to the 3',5' bis DMT product, because it is easier to separate from the desired 5'-mono DMT product. The 3'-DMT nucleosides and 5'-DMT nucleosides have very similar physical properties and are difficult to separate from one another. Furthermore, the 3' DMT product will for an active reagent in the next step, phosphitylation, and will not be easily separable at that stage, and thus will be incorporated into the desired oligonucleotide. Incorporation of the 3'-DMT nucleoside into an oligonucleotide results in an inverted orientation for the nucleoside within the oligomer. The oligomer containing the inverted nucleoside is difficult to separate from the desired product oligomer, due to their identical masses. The inverted nucleoside also makes the oligomer into which it is incorporated difficult to detect for the same reason.

In the process of forcing the 3'-DMT nucleoside to form the 3',5'-bis DMT nucleoside, a portion of the 5'-DMT (desired product) is also converted to the bis-DMT nucleoside product. As a result, the yield of purified 5'-DMT nucleoside is reduced substantially. Typically, yields of 70–80% of theory are the best to be expected. This reduction in yield is especially deleterious when using more expensive, modified nucleosides such as 2'-O-alkyl-ribonucleosides.

In some embodiments, the present invention presents a new set of synthetic conditions, e.g. a new class of activators, which give a much higher selectivity for the 5'- over the 3'-position. Because of this selectivity, the reaction can be controlled to go very near completion, with a minimal excess of DMT chloride, and with no detectable 3'-mono DMT produced during the reaction. Some 3',5'-bis DMT product may be formed from the 5' product under these conditions, but it is much easier to control and minimize. Since the resulting 5'-mono DMT product is of much higher purity compared to that produced by previously known processes, the purification method can be simplified. In particular embodiments of the present invention, greater than 99% purity is obtained without column chromatography, and with a chemical yield of 95% or greater. The inventive method is also scalable to production levels. Taken all together, the method of the present invention permits the user to produce selectively blocked nucleosides at a substantially reduced cost, due to reduced consumption of both protecting reagent and nucleoside and a reduced purification burden.

The present inventors have surprisingly found that, by replacing the solvent/base pyridine with an ortho substituted pyridine (such as 2,6-dimethylpyridine; also called 2,6-lutidine) as the solvent/base, or as the base plus a polar, aprotic solvent such as acetonitrile, the resulting reaction rate is much greater, as is the selectivity for the 5'-primary hydroxyl group. Lutidine is slightly more basic than pyridine, but other, more basic, materials such as dimethylaminopyridine do not give greater selectivity, although the reaction is faster than with pyridine. Lutidine is also more hindered than pyridine, yet other hindered bases such as triethylamine or diisopropylethylamine do not give more selectivity.

A putative reaction scheme for the hindered aryl base-activated (e.g. lutidine-activated) tritylation of an exemplary nucleoside according to the present invention is depicted in Scheme A, below.

The DMT reaction is generally thought to be an SN1 type, in which the chloride anion separates from the trityl (DMT) cation. The trityl cation is then trapped by available nucleophiles such as the 5' hydroxyl group. It is believed that the base scavenges the generated hydrogen chloride and thus allows the reaction equilibrium to shift towards completion. While not wishing to be bound by theory, it is thought that there is a transient complex formed between the trityl cation and the base, which complex is attacked by the nucleophilic hydroxyl group. As the approach of the nucleophile to the complex depends on steric factors, and as the ortho substitutions of lutidine flank the junction of the nitrogen of lutidine and the trityl cation, it is believed that this more hindered complex leads to greater selectivity for nucleophilic attack of a primary hydroxyl (e.g. 5'-OH) over a secondary hydroxyl (e.g. 3'- or 2'-) hydroxyl. It is also reasonable to expected that other similarly hindered aryl amines, e.g. other ortho-substituted pyridines, will confer the same advantages.

With this selectivity, the reaction's progress can be controlled by varying the equivalents of the reagents and the temperature. At ambient temperature, the reaction will progress to completion in less than 30 minutes as opposed to the reaction using pyridine, which takes a full day. To slow down the reaction enough to allow monitoring by TLC or HPLC, the reaction can be cooled down to a point at which the reaction takes up to several hours to complete (e.g. −10° C.). To prevent the formation of bis DMT product, the molar equivalents of DMT chloride can be held to less than 1.0. Any remaining unprotected nucleoside is easily extracted away in aqueous washes. To optimize the yield versus purity, various factors may be balanced, including the cost of the protecting group, the cost of the nucleoside to be protected, desired purity, etc.

Scheme A

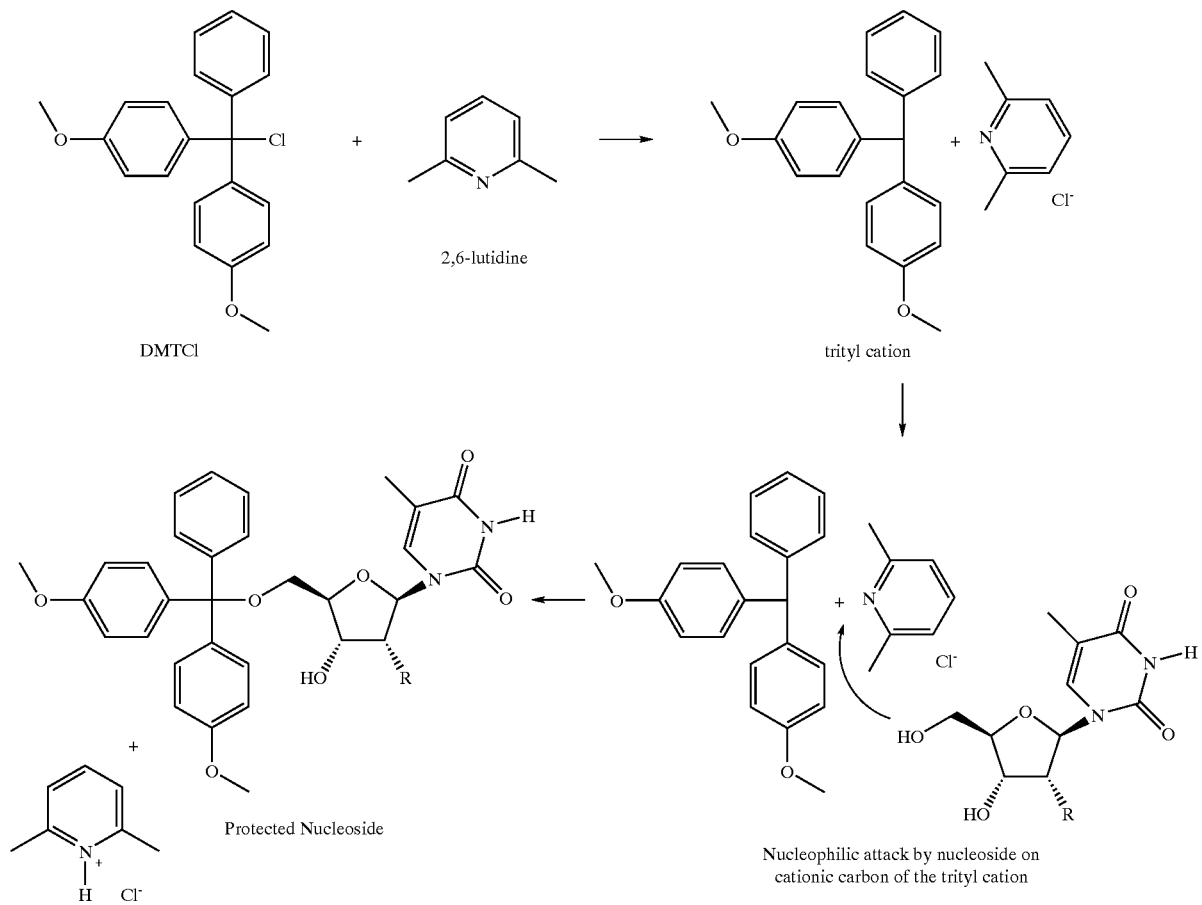

In some embodiments of the present invention, after quenching the reaction with methanol and the aqueous work-up, one is left with a mixture of mostly desired product, and 0.5–2% each of the following: bis DMT product, DMT methyl ether and DMT alcohol. While none of these impurities is harmful in the final phosphitylation reaction, it is advantageous to minimize them. In some embodiments of the invention, e.g. in the case of thymidine/uridine derivatives (which can be later converted to cytidine derivatives), the present invention provides at least two ways to purify the product without chromatography, or with only a very high-load, short-path chromatography column.

Embodiments of a first purification scheme according to the present invention involve base extraction. Because there is no detectable 3' mono DMT product, the physical properties of the remaining impurities are sufficiently different to allow the base extraction method to give acceptably pure product. For example in the case of MOE T, described in more detail below, the N-3 proton is acidic enough (~pK 10) to be completely ionized in the presence of a sodium hydroxide solution. Using the right conditions and solvents, the product, despite the lipophilic DMT group, can be extracted from an organic phase, such as toluene, into the basic aqueous phase. The DMT by-products, and to a lesser extent the bis DMT product, remain in the organic phase and are thus separated from the desired 5'-O-DMT protected product. The aqueous phase can then be acidified using a weak acid, and the desired product can then be extracted back into a fresh organic phase. The resulting product may have traces of bis DMT product if the reaction was pushed to near completion. Note that it is also possible to form a salt of the desired product (e.g. sodium hydride in tetrahydrofuran solvent) and filter the resulting solid from the organic solvent, thereby washing away impurities that cannot form an insoluble salt.

Products produced by the first purification scheme can be converted into other protected nucleosides by art-recognized means. They can also be converted into phosphitylating agents, such as phosphoramidites (amidites) by art-recognized methods, such as those described by Köster et al., infra. The resulting amidites can themselves be employed in an automated synthesis scheme, such as are described by Köster et al., infra.

Embodiments of the second purification method involve more steps than the first, but yield an even cleaner product. Only the desired product in the product mixture has a reactive hydroxyl group capable of nucleophilic attack. The second purification method takes advantage of this by reacting it with a di-functional agents, such as succinic anhydride. (Cyclic anhydrides are considered di-functional in this context, as they are condensed diacids, which upon reaction with nucleophiles, open to form an acid joined to the nucleophile via a carbonyl (—CO—) bond). This is commonly done as a method of linking the first nucleoside in an oligonucleotide to a solid support. The reaction is high yielding. The product contains a terminal ionizable group, e.g. a carboxylic acid, that can be ionized and solubilized in a dilute aqueous solution. The pH of the solution should be chosen to optimally ionize the ionizable groups and not ionize the N-3 hydrogen on the base. In the case where the terminal ionizable group is a carboxylic acid, this is most easily accomplished by adding one molar equivalent (e.g. about 0.9 to about 1.1 molar equivalent, more preferably about 0.95 to about 1.05 molar equivalent) of sodium hydroxide solution. After extraction into the aqueous layer from an organic layer, the impurities and any unreacted 3' hydroxyl product remain in the organic phase. The aqueous layer can be re-acidified and the product extracted back into a fresh organic layer as before. The resulting succinate product is useful by itself, or it can serve as a protecting group for the 3' hydroxyl during conversion of the thymidine derivative to a cytidine derivative, or the succinate group can be cleanly removed by nucleophilic base treatment such as ammonium hydroxide or methylamine. The resulting product has a purity of greater than 99.7%.

The second purification method is especially useful for purifying protected nucleosides that lack an acidic ring nitrogen in the nucleobase. It is also especially desirable when the protected nucleoside is to be used as the primer for a primer support. The terminal ionizable group (e.g. terminal succinate) may be covalently linked to a typical solid support, such as those described herein. The resulting primer support can be used in an automated synthesis scheme, such as described by Köster et al., infra.

The present invention provides a method for protecting an —OH group of a nucleoside. In particular embodiments, the present invention provides for protection of the 5'-O-position of a nucleoside. The present invention utilizes an activator that is generally described as a hindered aryl amine. While not wishing to be bound by theory, the inventors postulate that the hindered character of the hindered aryl amine tends to prevent attack by secondary hydroxyl groups on the cationic-amine complex formed in solution, as described above, thereby rendering the subsequent nucleophilic substitution by the primary 5'-OH group extremely favored. In this context, it is understood that "hindered" refers to the structural features near the aryl nitrogen. While alkyl groups are preferred as structural features that provide the hindered character of the aryl amine, one skilled in the art will recognize that other features, including alkenyl, alkynyl, cycloalkyl, and cycloalkenyl rings will also result in sufficient hindrance to 2'-OH attack on the cation-amine complex to render the reaction selective for primary OH groups, such as the 5'-OH group of a nucleoside. While excessive hindrance can lead to slow reaction progress, and is therefore not preferred, the person skilled in the art will recognize that greater hindrance will improve selectivity for the primary OH, notwithstanding the unfavorable kinetics of such hindrance.

Preferred hindered aryl amines according to the present invention have the following structure:

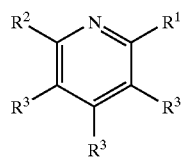

wherein each or $R^1$ and $R^2$ is H, alkyl or substituted alkyl, at least one of $R^1$ and $R^2$ being other than H, and each $R^3$ is independently H, alkyl, or substituted alkyl, or two adjacent $R^3$ moieties may be taken together to form a fused aromatic, aliphatic, or unsaturated aliphatic ring.

The term alkyl, unless otherwise defined herein, refers to a straight- or branched-chain aliphatic hydrocarbon of length $C_1$–$C_{12}$, more preferably $C_1$–$C_6$ and even more preferably, $C_1$–$C_4$. Suitable alkyl groups include methyl, ethyl, isopropyl, n-propyl, n-butyl, t-butyl, s-butyl and i-butyl.

Suitable alkyl substituent groups include unsaturated hydrocarbon moieties, such as alkenes and alkynes, as well as groups that are unreactive in the protection reaction, such as alkoxy groups (e.g. methoxy, ethoxy, etc.) alkylthio groups (e.g. Me-S—, Et-S, etc.), etc.

Suitable cycloalkyl and cycloalkenyl groups include $C_3$–$C_6$, preferably $C_3$–$C_5$ cycloalkyl and cycloalkenyl groups.

Suitable aliphatic rings represented by adjacent $R^3$ moieties that are joined to form a ring include cyclobuteno, cyclopenteno, cyclohexeno, cyclohepteno (the single unsaturation being in the pyridine ring to which the cycloaliphatic ring is fused). Suitable unsaturated aliphatic rings represented by adjacent $R^3$ moieties include cyclobutadieno, cyclopentadieno, cyclohexadieno, cycloheptadieno, (one unsaturation being in the fused pyridine ring, the other being in the aliphatic ring itself). Suitable aromatic rings represented by adjacent $R^3$ moieties include benzo, naphtho, and pyrido rings.

Preferred embodiments of the hindered aryl amine activator include 2,6-lutidine, 2-ethyl-6-methylpyridine and 2,6-diethylpyridine.

Protecting groups to be added by the inventive method include the optionally substituted trityl and optionally substituted pixyl and thiopixyl groups below.

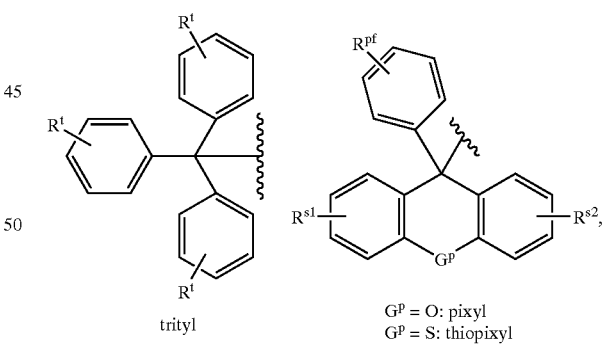

wherein each $R^t$ is H or a substituent, and each of $R^{pf}$, $R^{s1}$ and $R^{s2}$ are H or a substituent group. Suitable substituent groups represented by $R^t$ include alkoxy groups, such as methoxy. In particular embodiments according to the present invention, one or two of $R^t$ are methoxy, the remaining $R^t$ being H. Thus, preferred protecting groups according to the present invention include 4-methoxytrityl and 4,4'-dimethoxy trityl groups.

Regents for introducing the protecting groups (protecting reagents) include those represented by the formulas:

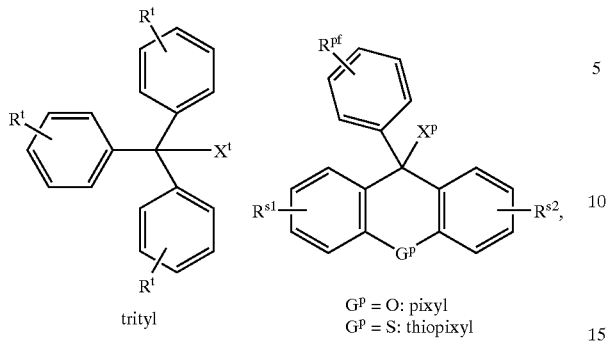

trityl $G^p$ = O: pixyl
$G^p$ = S: thiopixyl wherein $R^t$, $R^{pf}$, $R^{s1}$, and $R^{s2}$ are as defined above, and $X^p$ and $X^t$ are leaving groups. Suitable leaving groups include the halides, such as Cl and Br. Particular protecting reagents suitable for introducing trityl protecting groups according to the inventive methods include 4,4'-dimethoxytrityl chloride (DMTCl) and 4-methoxytrityl chloride (MMTCl). Particular protecting reagents suitable for introducing pixyl protecting groups according to the present invention include 9-phenyl-9-chloropixyl, 9-phenyl-9-chlorothiopixyl, etc.

Nucleosides to be protected by methods according to the present invention include nucleosides of the formula:

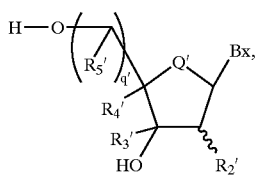

wherein $B_x$ is a nucleobase; $R_{2'}$ is H, OH, reversibly protected OH, a 2'-substitutent, or together with $R_{4'}$ forms a bridge; $R_{3'}$ is H or a substituent; $R_{4'}$ is H, alkyl, substituted alkyl, or together with $R_{2'}$ or $R_{5'}$ forms a bridge; $R_{5'}$ is H or together with $R_{4'}$ forms a bridge; Q' is O, S, NH, N-alkyl, $CH_2$; and q' is 0 or 1.

Particular nucleosides to be protected by the method according to the present invention include nucleosides of the formula:

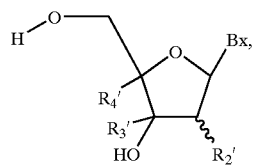

wherein $R_{2'}$ is H, OH, reversibly protected OH, a 2'-substitutent, or together with $R_{4'}$ forms a bridge; $R_{3'}$ is H or a substituent; $R_{4'}$ is H, alkyl, substituted alkyl, or together with $R_{2'}$ forms a ring. More specific nucleosides to be protected according to the present invention include those in which $R_{2'}$ is H or a substituent, or together with $R_{4'}$ forms a bridge; $R_{3'}$ is H, $R_{4'}$ is H or together with $R_{2'}$ forms a bridge. Particular values of $R_{2'}$ that may be mentioned are H and methoxyethoxy. Other suitable substituents, especially those represented by $R_{2'}$–$R_{4'}$ as well as $B_x$ are defined further herein.

In particular aspects of the invention, the nucleosides to be protected are pyrimidine nucleosides such as compounds represented by the formula:

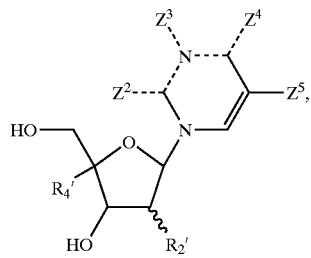

wherein $R_{2'}$ and $R_{4'}$ are as defined herein;

$Z^2$ is $NH_2$ or O;

$Z^3$ is absent or is H;

Z is $NH_2$, O, or together with $Z^5$ forms a ring, which may optionally be fused to one or more additional rings, and which optionally may be further substituted;

$Z^5$ is H, a ring substituent, or together with $Z^5$ form a ring, which may optionally be fused to one or more additional rings, and which optionally may be further substituted; and the dashed lines (———) indicate single, double or aryl bonds, or tautomeric equivalents thereof.

Ring substituents represented by $Z^5$ include alkyl, such as methyl and ethyl, alkynyl, such as propynyl, butynyl, pentynyl, substituted alkyl, such as aminoalkyl and hydroxyalkyl, and substituted alkynyl, such as phenylpropynyl.

Rings and ring systems represented by $Z^4$ and $Z^5$, taken together with the pyrimidine ring, include G-clamps, cytosine analogs and phenoxazines, as described in more detail herein, especially those in which $Z^4$ and $Z^5$ together form the following ring systems:

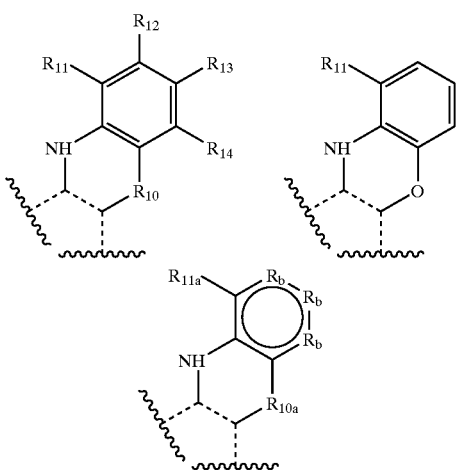

wherein the variables $R_{10}$–$R_{14}$, $R_{10a}$, $R_{11a}$, and $R_b$ are defined in more detail in the section titled G-clamps, Cytidine analogs and Phenoxazines, herein, the dashed lines indicate single or double bonds, and the squiggles (∿) indicate the points of fusion of the ring system to the pyrimidine ring.

Further optional substituents on the ring or ring system formed by $Z^4$ and $Z^5$, taken together, include those represented by $R_{11}$–$R_{14}$, $R_{10a}$ and $R_{11a}$, as described in more detail herein.

Particular embodiments represented by the foregoing nucleosides include cytidine (C), 5-methylcytidine (5-Me C), 5-propynylcytidine (5-propynyl-C), 5-propynyl-2'-O-methoxyethylcytidine (5-propynyl-MOE C), 5-propyny-2'-deoxycytidine (5-propynyl-dC), 5-propynylthymidine (5-propynyl-T), 5-propynyl-2'-O-methoxyethyluridine, 2'-deoxycytidine (dC), 2'-deoxy-5-methylcytidine (5-Me dC), 2'-O-methoxyethylcytidine (MOE C), 5-methyl-2'-O-methoxyethylcytidine (5-Me MOE C), thymidine (dT), uridine (U), 5-methyluridine (5-Me U), 2'-methoxyethyl-5-methyluridine (MOE T).

Nucleosides having an $N^3$—H that is susceptible of ionization in basic solution are especially preferred. These include compounds having the formula:

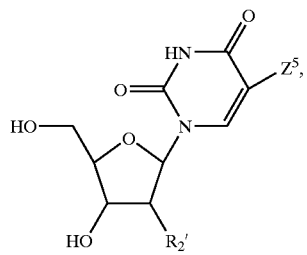

wherein $R_{2'}$ and $Z^5$ have the meanings defined herein. Especially preferred nucleosides according to the invention include those in which $R_{2'}$ is H, OH, protected OH, or a 2'-substituent and $Z^5$ is H, alkyl or alkynyl. Preferred values of $Z^5$ are methyl, ethyl, propyl and propynyl. Other preferred nucleosides include those in which $R_{2'}$ is —O-Alkyl, wherein the alkyl is optionally substituted, e.g. with an —O-Alkyl group. In this context, Alkyl is a hydrocarbon chain, which may be branched, having from 1 to about 10 carbon atoms. Especially preferred $R_2$ groups include —OCH$_3$, —OCH$_2$CH$_3$, and —O—CH$_2$CH$_2$—O—CH$_3$. Another preferred value of $R_{2'}$ is H.

Protected nucleosides that may be made by the process of the present invention include:

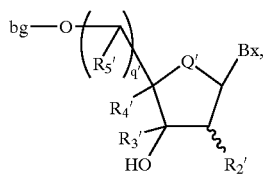

wherein $B_x$ is a nucleobase; $R_{2'}$ is H, OH, reversibly protected OH, a 2'-substitutent, or together with $R_{4'}$ forms a bridge; $R_{3'}$ is H or a substituent; $R_{4'}$ is H, alkyl, substituted alkyl, or together with $R_{2'}$, or $R_{5'}$ forms a bridge; $R_{5'}$ is H or together with $R_{4'}$ forms a bridge; Q' is O, S, NH, N-alkyl, CH$_2$; q' is 0 or 1, and bg is a protecting group. In particular embodiments of the present invention, bg is an optionally substituted trityl group, an optionally substituted pixyl group, or an optionally substituted thiopixyl group, each as described further herein.

In particular embodiments of the present invention, the protected nucleoside made by the inventive process include those represented by the formula:

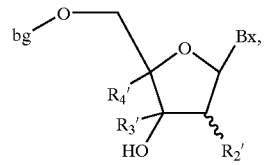

wherein $R_{2'}$ is H, OH, reversibly protected OH, a 2'-substitutent, or together with $R_{4'}$ forms a bridge; $R_{3'}$ is H or a substituent; $R_{4'}$ is H, alkyl, substituted alkyl, or together with $R_{2'}$ forms a ring, and bg is a protecting group. In particular embodiments, bg is an optionally substituted trityl group, an optionally substituted pixyl group, or an optionally substituted thiopixyl group. In specific embodiments, bg is a substituted trityl group selected from 4-methoxytrityl and 4,4'-dimethoxytrityl.

In particular embodiments of the present invention, protected nucleosides produced by the inventive methods include:

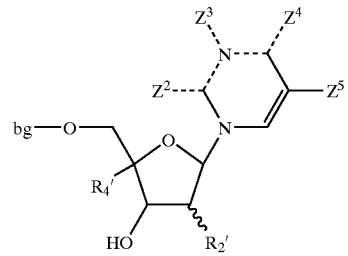

wherein bg, $R_{2'}$, $R_{4'}$, $Z^2$–$Z^5$ are defined above in regard to the nucleosides amenable to the present invention. Specific blocked nucleosides according to the present invention include compounds of the formula:

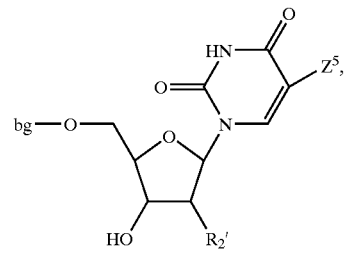

wherein bg, $R_{2'}$, and $Z^5$ are defined above with regard to nucleosides amenable to the present invention.

The nucleoside to be protected, the protecting reagent and the activator may be combined neat, or they may be combined in a suitable solvent, such as a polar organic solvent, e.g. dimethylformamide, acetonitrile or pyridine.

Protected nucleosides having an ionizable group, such as the $N^3$—H of thymidine or uracil, may be extracted directly into basic aqueous solution from a first organic phase comprising the protected nucleoside and activator. In some embodiments, the first organic phase further comprises a water-immiscible organic solvent, such as toluene, alkyl alkylates (ethyl acetate), or mixtures thereof, which water-immiscible organic solvent is added before contacting the first organic phase with the basic aqueous phase. Other water-immiscible organic solvents that may be mentioned include xylenes, hexanes, heptane, etc. The pH of the basic organic phase should be above about 9, in particular in the range of about 9 to 16, even more particularly in the range of about 9 to about 14, e.g. about 9 to about 11. In this range, the $N^3$ of thymidine or uracil will be ionized, and the protected nucleoside will partition into the basic aqueous phase, while the less polar side products will tend to remain in the organic phase. After the first organic phase and the basic aqueous phase have been contacted for a time and under conditions suitable for obtaining mass transfer between the two phases (e.g. by mixing, stirring, etc.), they are permitted to settle and are separated from one another.

The desired product, protected nucleoside, remains in the aqueous phase, which is then re-acidified with a suitable acid. Suitable acids include any acid capable of reducing the pH to about 5. Particularly suitable acids include citric acid, acetic acid, substituted acetic acids, mineral acids, such as phosphoric acid, etc. It is important that the pH be kept above about 4.5, therefore citric acid is preferred, however the person skilled in the art will recognize that other acids may be used so long as one is careful to maintain the pH above about 4.5, lest the pH drop low enough to remove some of the acid-labile protecting group.

Once the aqueous phase has been re-acidified, it is contacted with a second organic phase. It is preferred that the second organic phase contain sufficient water-immiscible solvent to prevent the protected nucleoside from forming a gum that will precipitate out of solution. The aforementioned water-immiscible solvents may be used.

The protected nucleosides according to the present invention may be phosphitylated according to art-recognized procedures, such as those taught by Köster et al., infra. In general, a nucleoside may be reacted with a phosphorodiamidite in the presence of a suitable activator, and optionally in a suitable solvent, as discussed in more detail herein and in Köster et al. Suitable phosphitylating reagents are depicted as formula (5), below, and the resulting phosphoramidites (amidites) are represented by formula (6), below.

Protected nucleosides according to the present invention may also be derivatized using a di-functional group, such as a diacid group or a diacid anhydride. Exemplary derivatized nucleosides of the present invention are depicted in the formula below:

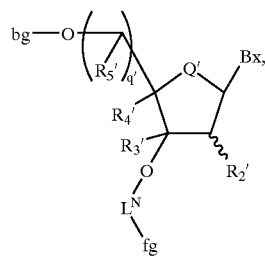

wherein the variables, $R_2$'–$R_5$', q', Q', bg and $B_x$ are defined above, $L^N$ is a linking group, and fg is a functional group. Particular values for fg include the carboxylic acid functionality, as well as acid derivatives (e.g. acid halides and anhydrides). The acid functional groups are preferred in that they are generally stable and ionizable in aqueous solution. The linking groups $L^N$ is e.g. an alkylcarbonyl function, e.g. —$COCH_2$—, —$COCH_2CH_2$—, —$COCH_2CH_2CH_2$—, etc. Suitable derivatizing reagents (that is reagents for introducing the derivatizing group into the protected nucleoside) include compounds represented by the formula: $X^L$—$L^N$—fg, wherein $X^L$ is a suitable leaving group such as a halide, an a carbonyloxy group (e.g. $CH_3CO$—, $CH_3CH_2CO$—, etc.) or OH. Especially suitable derivatizing reagents include diacids, such as succinic acid, and diacid anhydrides, such as succinic anhydride. Other suitable acids include malonic, glutaric, adipic and pimelic acid. Suitable anhydrides include malonic anhydride, glutaric anhydride, adipic anhydride and pimelic anhydride. In this regard, $B_x$ may be any suitable base, as the method provides fg, which is ionizable, and therefore does not require the presence of an ionizable group on the nucleobase itself. Accordingly, $B_x$ may be a purine (e.g. A or G), a protected purine, a pyrimidine (C, U, T), a protected pyrimidine, a 5-methylated pyrimidine, a 5-propynylated pyrimidine, a 9-propynyl-9-deaza-8-azapurine, or any of the other numerous nucleobases set forth herein.

In embodiments of the invention, fg provides an ionizable group that will allow the derivatized protected nucleoside to be extracted into aqueous base, irrespective of whether or not there is an ionizable ring nitrogen on the nucleobase, $B_x$. The derivatized nucleoside is first prepared in an organic phase, which preferably contains some water-immiscible organic solvent, and is extracted into basic aqueous solution. In some embodiments, it is sufficient to dissolve one equivalent of a strong base, e.g. an alkali hydroxide such as sodium hydroxide (relative to the protected nucleoside) in water for use as the basic aqueous phase. In other embodiments, the pH may be adjusted to a pH in the range of about 8 to about 10.

The protected derivatized nucleoside partitions into the basic aqueous phase, leaving side products behind in the organic phase. Once the two phases have been separated, the basic aqueous phase may then re-acidified, again taking care not to lower the pH to below 4.5 (e.g. with an acid as set forth above), after which the protected derivatized nucleoside may extracted into a second organic phase. As an alternative, once the basic aqueous phase having a pH in the range of about 8 to about 10 has been separated from the first organic phase, its pH may be further increased to remove the functional group. Care must be taken, however, to avoid removing protecting groups, such as base protecting groups, that may be present on $B_x$.

If the second organic phase extraction is selected, the functional group fg may be used to bind the nucleoside to a support, such as a solid support, e.g. controlled pore glass (CPG) or a polymer support, as described in more detail herein. Alternatively, the group $L^N$—fg may be removed, e.g. by reacting the nucleoside with a nucleophilic base, e.g. ammonium hydroxide or methylamine. This reaction produces a purified protected nucleoside. The resulting purified protected nucleoside may then be phosphitylated with a suitable phosphitylating agent as described herein (e.g. formula (5)) to produce an amidite as described herein (e.g. formula (6)).

The person skilled in the art will recognize that the derivatization and purification protocol as set forth herein is readily generalizable to all sorts of protected nucleosides, and provides a convenient method for making either primer support or amidites at the discretion of the user.

The present invention contemplates manufacture of protected nucleosides for use in the manufacture of oligonucleotides. Such oligonucleotides may be manufactured by the phosphoramidite method as previously mentioned. Alternatively, oligonucleotides may be manufactured from protected nucleosides using any art-recognized method, including the phosphotriester approach and the H-phosphonate approach as described in the literature. Such oligonucleotides can be used as antisense compounds, as primers or probes for used in nucleic acid amplification schemes, as diagnostics, as affinity probes for use on affinity columns, etc. They may also be derivatized to make "oligomers," as described below.

In the context of the invention, the terms "oligomeric compound" and "oligomer" refer to a polymeric structure capable of hybridizing a region of a nucleic acid molecule (e.g. DNA, RNA or derivative). Each oligomer comprises a plurality of monomer subunits, and each monomer subunit in turn comprises a binding member and a backbone. The function of the binding member is to provide sequence-specific binding to a target oligo- or polynucleotide. These interactions may be Watson-Crick hybridization, Hoogsteen base pairing, a combination of these mechanisms, or some other sequence-specific interaction.

The function of the backbone is to hold the binding members in a spatial configuration amenable to sequence-specific binding. In general, the backbone comprises a skeletal member and a linking member. The skeletal member generally has separate sites to which the binding member and the linking member (linker) are bound. The linker joins skeletal members of adjacent monomer subunits, thereby establishing the sequence of the monomers.

In naturally occurring RNA, the binding member is a nucleosidic base, and the backbone comprises a sugar residue and a phosphate. The sugar residue, ribosyl, acts as the skeletal member, while the phosphate joins adjacent monomers through the 5'- and 3'-oxygen atoms on the ribosyl ring. The sugar is also bound to the nucleosidic base (base) at the 1'-position, the -β-D configuration predominating.

Naturally occurring DNA is analogous to RNA, except that the sugar is a 2'-deoxyribosyl.

Various combinations of binding member and backbone are known in the art. Together a binding member and a backbone form a monomeric subunit. Various types of monomeric subunits will be discussed in detail below.

As alluded above, one type of monomeric subunit known in the art is a nucleotide, which is a base-sugar-phosphate combination. The base portion of the nucleoside is normally a heterocyclic base moiety, also called a nucleobase. The two most common classes of such heterocyclic bases are purines and pyrimidines. The naturally occurring purine bases are guanine (G) and adenine (A), which are linked to the sugar through the 9-N nitrogen in the β-anomeric position on the sugar ring. The naturally occurring pyrimidine bases are uracil (U), thymine (T) and cytidine (C), which are linked to the sugar through the 1-N nitrogen. In DNA, Watson-Crick base pairing occurs between G and C, and between A and T, whereas in RNA, Watson-Crick base pairing occurs between G and C, and between A and U. The Watson-Crick base pairs for DNA and RNA are shown below.

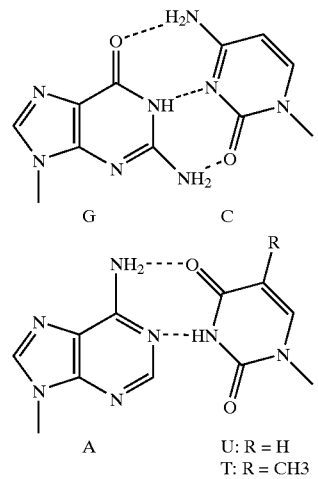

In synthetic oligonucleotides, such as antisense therapeutics and diagnostics, one or more of the naturally occurring nucleobases may be replaced by an analogous binding member (nucleobase analog). Hereinafter, nucleobases and their analogs will be referred to collectively as bases. In general, a nucleobase analog is a moiety that behaves like a nucleobase by providing sequence-specific binding to a target. Such binding generally occurs by hydrogen bonding between nucleobase ring constituents and/or exocyclic substituents, and may be analogous to Watson-Crick bonding, Hoogsteen bonding, some combination thereof, or some other regime.

In naturally occurring oligonucleotides, the sugar ring is β-D-ribosyl (RNA) or β-D-2'-deoxyribosyl (DNA). As alluded above, the hybridization behavior of DNA with RNA differs from the hybridization of RNA to RNA. This difference gives rise to different in vitro and in vivo effects. For example, DNA-RNA hybrids effectively bind to RNAse H, which results in scission of RNA. In contrast, RNA-RNA hybrids may be unwound by helicase, whereby the antisense strand is permitted to form a hybrid with mRNA. The exogenous RNA-mRNA hybrid interacts with one or more members of the RISC complex, which effects mRNA scission.

Synthetic sugars and sugar analogs are designed to adopt certain spatial conformations that resemble DNA, RNA or some structure intermediate between these conformations. Again, the sugar or sugar analog functions as a sort of platform to hold the base in the correct orientation to interact with bases on the opposite strand. The sugar or sugar analog (collectively skeletal members) also provides binding sites for the linking groups, which join the monomeric units together to form the oligomer. The conformation of the sugar or sugar analog greatly influences the spatial orientations of the bases and linking groups, and also greatly influences the shape of the antisense-sense hybrid in solution. This conformational influence can have an important impact on the efficacy of the antisense compound in modulation of gene expression.

Naturally occurring nucleosides are linked to one another via a phosphoryl diester linker. Antisense compounds may be prepared using phosphoryl diester linkers, which are generally suitable for diagnostic and other nuclease-free uses. However, antisense therapeutic compounds advantageously comprise at least one phosphorothioate linker, owing to the latter's superior nuclease stability. Both phosphoryl and phosphorothioate linkers are generally referred to as phosphate diester linkers. When a plurality of nucleosides are linked by successive phosphate diester linkers, the resulting oligomer is called an oligonucleotide.

As alluded above, synthetic oligonucleotides may be modified extensively from their natural form for use in antisense therapeutics. The most commonly occurring modifications include the phosphorothioate backbone, the presence of various substituents on the sugar moiety, and modification of bases. Many of these variations will be discussed below.

Sugar Modifications

Some oligonucleotides that may be made using protected nucleosides, which have been made by methods of the present invention, are represented by formula I:

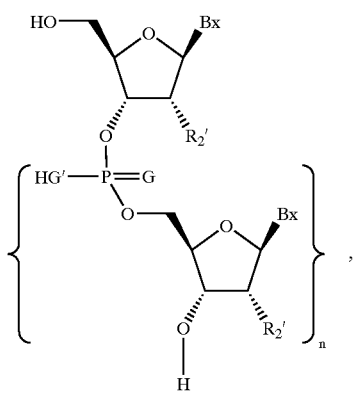

(1)

or tautomers, salts or solvates thereof. In formula 1, each G and G' is independently O or S, each $R_{2'}$ is independently H or OH, n is an integer and each Bx is independently a nucleobase as described in greater detail herein. Thus the repeating backbone unit is a ribosyl ring linked to a phosphate or phosphorothioate linker. Selectivity for a particular target sequence is achieved by modification of the sequence of Bx units. This procedure is discussed in greater detail herein.

The 2'-position may be H (i.e. 2'-deoxyribosyl) or OH (ribosyl). While it is possible for all $R_2$ units to be OH, e.g. where the oligomers will be used in siRNA applications, it is often desirable for all or part of the oligomer to be 2'-deoxy. In preferred embodiments of the present invention, each of the $R_2$ groups is H. In other cases, a contiguous stretch sugars are 2'-deoxy, while one or more stretches of the remainder of the oligonucleotide contain ribosyl or 2'-modified ribosyl sugars, as described in more detail herein. It has been found that oligonucleotides containing a stretch of deoxy ribosyl nucleotides are able to recruit RNase H, as described in greater detail herein.

Formula 1 depicts the simplest oligonucleotides, which are also referred to in the art as "first generation" oligonucleotides. Other oligonucleotides are possible, and are encompassed within the meaning of "oligonucleotide" as used herein. In particular, oligonucleotides may contain repeating units where the standard ribosyl unit is replaced with a substituted ribosyl unit (e.g. a 2'-deoxy-2'-substituted ribosyl unit), where the ribosyl unit is replaced by a different sugar entirely (e.g. an arabinosyl or erythrosyl unit), or where the ribosyl unit is replaced by a bridged sugar unit. A formula representing oligonucleotides of this type is depicted in Formula 2.

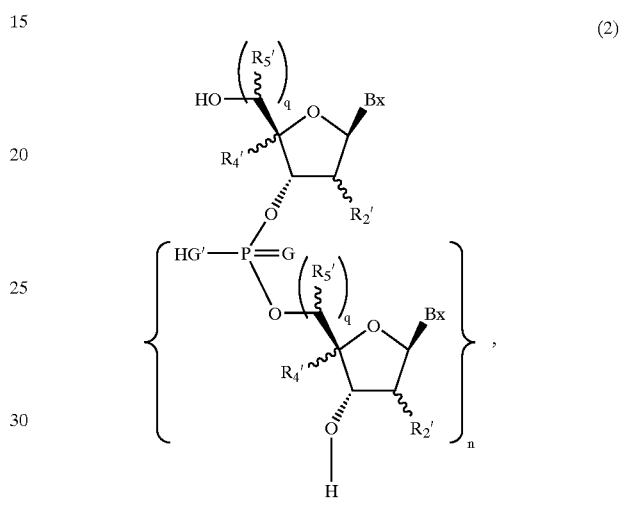

(2)

or tautomers, salts or solvates thereof. In formula 2, G, G', Bx and n have the same meanings as in formula 1. The squiggly lines (∼∼∼) ring indicate that the corresponding substituents may be in either the down or up configuration. The value of q may be 0 or 1. $R_{2'}$ may be H, OH, a reversibly protected OH, a 2'-substituent, or may form, together with $R_{4'}$, a bridge. $R_{4'}$ is either H or, together with $R_{2'}$ or $R_{5'}$, forms a bridge.

The person skilled in the art will recognize that when $R_{2'}$ is in the down configuration and q' is 1, the ring is a ribosyl ring, whereas when $R_{2'}$ is in the up configuration and q' is 1, the ring is an arabinosyl ring. Likewise, when q' is 0 and $R_2'$ is in the down configuration, the ring is an erythrosyl ring. When $R_2'$ and $R'_4$ are joined to form a bridge, the ring is called a locked nucleic acid (LNA), as described in greater detail herein. In some embodiments, the bridge formed by $R_2'$ and $R'_4$ is $R_2'$—O—$(CH_2)_r$—$R'_4$ (wherein r is 1 or 2) or $R_2'$—$CH_2$—O—$CH_2$—$R'_4$ (the use of $R_2'$ and $R'_4$ in the sub-formulae indicating the points of attachment.) LNA may be present in either α-L- or β-D-conformation. See Vester et al., "LNAzymes: Incorporation of LNA-Type Monomers into DNAzymes Markedly Increases RNA Cleavage," Journal of the American Chemical Society, 2002, 124, 13682–3. Each of these analogs possesses a number of useful characteristics, including resistance to exonuclease activity, induction if endonuclease activity (e.g. by RNAse H, the RISC complex, etc.) and modulation of hybridization.

When $R_{4'}$ and $R_{5'}$ form a bridge, they may form, along with the sugar ring to which they are attached, a tricyclic ring. Tricyclic nucleosides of the structure:

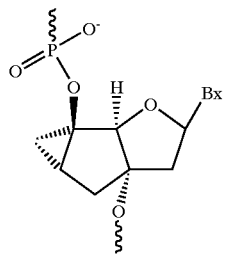

are described by Rennenberg et al. in Nucleic Acids Research, 30(13), 2751–7 (2002). One skilled in the art will recognize that the analogous phosphorothioates, and 2'-substituted tricyclic deoxynucleosides may be prepared by methods analogous to those taught by Rennenberg et al., as modified by the teaching herein. In particular, the phosphorothioates may be prepared by substituting a sulfurizing oxidant (such a phenyl acetyl disulfide) for the oxidizing agent taught by Rennenberg et al. The 2'-substituted tricyclic deoxynucleosides may be prepared from the analogous 2'-substituted deoxynucleosides, using a 2'-OH protecting group in the case of ribonucleic acid.

The variable Sug, as used herein, refers to a sugar ring or a modified sugar ring. Sugar rings include ribosyl, 2'-deoxyribosyl, arabinosyl, erythrosyl and other modified sugar rings, such as bicyclic and tricyclic ring systems. Modified sugar rings include the foregoing sugar rings as modified per the description herein, e.g. at the 2'-position, or by a bridge between the 2'- and 4'-positions as described in further detail herein.

Certain oligonucleotides that utilized arabino-pentofuranosyl nucleotides as building blocks have been described. Damha et. al., J.A.C.S., 1998, 120, 12976–12977; and Damha et. al., Bioconjugate Chem., 1999, 10, 299–305.

Suitable 2'-substituents corresponding to $R_2$, include: F, O-alkyl (e.g. O-methyl), S-alkyl, N-alkyl, O-alkenyl, S-alkenyl, N-alkenyl; O-alkynyl, S-alkynyl, N-alkynyl; O-alkyl-O-alkyl, wherein the alkyl, alkenyl and alkynyl may be substituted or unsubstituted $C_1$ to $C_{10}$ alkyl or $C_2$ to $C_{10}$ alkenyl or alkynyl, respectively. Particularly preferred are $O[(CH_2)_gO]_hCH_3$, $O(CH_2)_gOCH_3$, $O(CH_2)_gNH_2$, $O(CH_2)_gCH_3$, $O(CH_2)_gONH_2$, and $O(CH_2)_gON[(CH_2)_gCH_3]_2$, where g and h are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred 2'-modification is 2'-deoxy-2'-methoxyethoxy (2'-O—$CH_2CH_2OCH_3$, also known as 2'-O-(2-methoxyethyl) or 2'-MOE ribosyl) (Martin et al., Helv. Chim. Acta, 1995, 78, 486–504). Other preferred modifications include 2'-dimethylaminooxyethoxy, i.e., a $O(CH_2)_2ON(CH_3)_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other preferred modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide.

Further representative substituent groups include groups of formula $I_a$ or $II_a$:

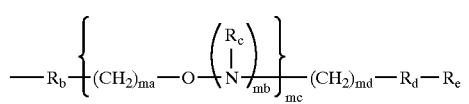

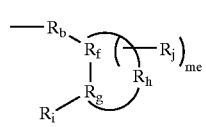

wherein:
$R_b$ is O, S or NH;
$R_d$ is a single bond, O or C(=O);
$R_e$ is $C_1$–$C_{10}$ alkyl, $N(R_k)(R_m)$, $N(R_k)(R_n)$, N=C($R_p$)($R_q$), N=C($R_p$)($R_r$) or has formula $III_a$;

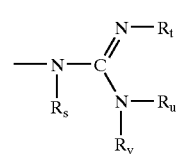

each $R_s$, $R_t$, $R_u$ and $R_v$ is, independently, hydrogen, C(O)$R_w$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_k$ is hydrogen, a nitrogen protecting group or —$R_x$—$R_y$;
$R_p$ is hydrogen, a nitrogen protecting group or —$R_x$—$R_y$;
$R_x$ is a bond or a linking moiety;
$R_y$ is a chemical functional group, a conjugate group or a solid support medium;

each $R_m$ and $R_n$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;

or $R_m$ and $R_n$, together, are a nitrogen protecting group, are joined in a ring structure that optionally includes an additional heteroatom selected from N and O or are a chemical functional group;

$R_i$ is $OR_z$, $SR_z$, or $N(R_z)_2$;

each $R_z$ is, independently, H, $C_1$–$C_8$ alkyl, $C_1$–$C_8$ haloalkyl, $C(=NH)N(H)R_u$, $C(=O)N(H)R_u$, or $OC(=O)N(H)R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)OR_k$, halo, $SR_k$ or CN;

$m_a$ is 1 to about 10;

each mb is, independently, 0 or 1;

mc is 0 or an integer from 1 to 10;

md is an integer from 1 to 10;

me is from 0, 1 or 2; and provided that when mc is 0, md is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety. Representative cyclic substituent groups of Formula II are disclosed in U.S. patent application Ser. No. 09/123,108, filed Jul. 27, 1998, entitled "RNA Targeted 2'-Modified Oligonucleotides that are Conformationally Preorganized," hereby incorporated by reference in its entirety.

Particularly preferred sugar substituent groups include $O[(CH_2)_gO]_hCH_3$, $O(CH_2)_gOCH_3$, $O(CH_2)_gNH_2$, $O(CH_2)_gCH_3$, $O(CH_2)_gONH_2$, and $O(CH_2)_gON[(CH_2)_gCH_3)]_2$, where g and h are from 1 to about 10.

Some preferred oligomeric compounds of the invention contain at least one nucleoside having one of the following substituent groups: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O—$CH_2CH_2OCH_3$, also known as 2'-O-(2-methoxyethyl) or 2'-MOE] (Martin et al., Helv. Chim. Acta, 1995, 78, 486), i.e., an alkoxyalkoxy group. A further preferred modification is 2'-dimethylaminooxyethoxy, i.e., a $O(CH_2)_2ON(CH_3)_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, entitled "Aminooxy-Functionalized Oligomers and Methods for Making Same;" hereby incorporated by reference in their entirety.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety. Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999, hereby incorporated by reference in its entirety. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligonucleotide structure, the phosphate groups are commonly referred to as forming the internucleoside linkages of the oligonucleotide. The normal internucleoside linkage of RNA and DNA is a 3' to 5' phosphodiester linkage.

While the present invention may be adapted to produce oligonucleotides for any desired end use (e.g. as probes for us in the polymerase chain reaction), one preferred use of the oligonucleotides is in antisense therapeutics. One mode of action that is often employed in antisense therapeutics is the so-called RNAse H mechanism, whereby a strand of DNA is introduced into a cell, where the DNA hybridizes to a strand of RNA. The DNA-RNA hybrid is recognized by an endonuclease, RNAse H, which cleaves the RNA strand. In normal cases, the RNA strand is messenger RNA (mRNA), which, after it has been cleaved, cannot be translated into the corresponding peptide or protein sequence in the ribosomes. In this way, DNA may be employed as an agent for modulating the expression of certain genes.

It has been found that by incorporating short stretches of DNA into an oligonucleotide, the RNAse H mechanism can be effectively used to modulate expression of target peptides or proteins. In some embodiments of the invention, an oligonucleotide incorporating a stretch of DNA and a stretch of RNA or 2'-modified RNA can be used to effectively modulate gene expression. In preferred embodiments, the oligonucleotide comprises a stretch of DNA flanked by two stretches of 2'-modified RNA. Preferred 2'-modifications include 2'-O-methyl and 2'-O-methoxyethyl as described herein.

The ribosyl sugar moiety has also been extensively studied to evaluate the effect its modification has on the properties of oligonucleotides relative to unmodified oligonucleotides. The 2'-position of the sugar moiety is one of the most studied sites for modification. Certain 2'-substituent groups have been shown to increase the lipohpilicity and enhance properties such as binding affinity to target RNA, chemical stability and nuclease resistance of oligonucleotides. Many of the modifications at the 2'-position that show enhanced binding affinity also force the sugar ring into the $C_3$-endo conformation.

RNA exists in what has been termed "A Form" geometry while DNA exists in "B Form" geometry. In general, RNA:RNA duplexes are more stable, or have higher melting temperatures (Tm) than DNA:DNA duplexes (Sanger et al., Principles of Nucleic Acid Structure, 1984, Springer-Verlag; New York, N.Y.; Lesnik et al., Biochemistry, 1995, 34, 10807–10815; Conte et al., Nucleic Acids Res., 1997, 25, 2627–2634). The increased stability of RNA has been attributed to several structural features, most notably the improved base stacking interactions that result from an A-form geometry (Searle et al., Nucleic Acids Res., 1993, 21, 2051–2056). The presence of the 2' hydroxyl in RNA biases the sugar toward a C3' endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). In addition, the 2' hydroxyl groups of RNA can form a network of water mediated hydrogen bonds that help stabilize the RNA duplex (Egli et al., Biochemistry, 1996, 35, 8489–8494).

DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051–2056). The structure of a hybrid duplex is intermediate between A- and B-form geometries, which may result in poor stacking interactions (Lane et al., Eur. J. Biochem., 1993, 215, 297–306; Fedoroff et al., J. Mol. Biol., 1993, 233, 509–523; Gonzalez et al., Biochemistry, 1995, 34, 4969–4982; Horton et al., J. Mol. Biol., 1996, 264, 521–533). The stability of a DNA:RNA hybrid is central to antisense therapies as the mechanism requires the binding of a modified DNA strand to a mRNA strand. To effectively inhibit the mRNA, the antisense DNA should have a very high binding affinity with the mRNA. Otherwise the desired interaction between the DNA and target mRNA strand will occur infrequently, thereby decreasing the efficacy of the antisense oligonucleotide.

Various synthetic modifications have been proposed to increase nuclease resistance, or to enhance the affinity of the antisense strand for its target mRNA (Crooke et al., Med. Res. Rev., 1996, 16, 319–344; De Mesmaeker et al., Acc. Chem. Res., 1995, 28, 366–374). A variety of modified phosphorus-containing linkages have been studied as replacements for the natural, readily cleaved phosphodiester linkage in oligonucleotides. In general, most of them, such as the phosphorothioate, phosphoramidates, phosphonates and phosphorodithioates all result in oligonucleotides with reduced binding to complementary targets and decreased hybrid stability.

One synthetic 2'-modification that imparts increased nuclease resistance and a very high binding affinity to nucleotides is the 2'-methoxyethoxy (MOE, 2'-OCH$_2$CH$_2$OCH$_3$) side chain (Baker et al., J. Biol. Chem., 1997, 272, 11944–12000; Freier et al., Nucleic Acids Res., 1997, 25, 4429–4443). One of the immediate advantages of the MOE substitution is the improvement in binding affinity, which is greater than many similar 2' modifications such as O-methyl, O-propyl, and O-aminopropyl (Freier and Altmann, Nucleic Acids Research, (1997) 25:4429–4443). 2'-O-methoxyethyl-substituted oligonucleotides also have been shown to be antisense inhibitors of gene expression with promising features for in vivo use (Martin, P., Helv. Chim. Acta, 1995, 78, 486–504; Altmann et al., Chimia, 1996, 50, 168–176; Altmann et al., Biochem. Soc. Trans., 1996, 24, 630–637; and Altmann et al., Nucleosides Nucleotides, 1997, 16, 917–926). Relative to DNA, they display improved RNA affinity and higher nuclease resistance. Chimeric oligonucleotides with 2'-O-methoxyethyl-ribonucleoside wings and a central DNA-phosphorothioate window also have been shown to effectively reduce the growth of tumors in animal models at low doses. MOE substituted oligonucleotides have shown outstanding promise as antisense agents in several disease states. One such MOE substituted oligonucleotide is presently being investigated in clinical trials for the treatment of CMV retinitis.

LNAs (oligonucleotides wherein the 2' and 4' positions are connected by a bridge) also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. LNAs may be in either the α-L- or the β-D-conformation. Vester et al., J.A.C.S, 124 (2002) 13682–13683.

LNAs in which the 2'-hydroxyl group is linked to the 4' carbon atom of the sugar ring thereby forming a 2'-C,4'-C-oxymethylene linkage thereby forming a bicyclic sugar moiety. The linkage is preferably an alkylene (—CH$_2$—)$_n$ group bridging the 2' oxygen atom and the 4' carbon atom wherein n is 1 or 2 (Singh et al., Chem. Commun., 1998, 4, 455–456). LNA and LNA analogs display very high duplex thermal stabilities with complementary DNA and RNA (Tm=+3 to +10 C), stability towards 3'-exonucleolytic degradation and good solubility properties. Other preferred bridge groups include the 2'-CH$_2$OCH$_2$-4' bridge.

Bases

The term "nucleobase," as used herein, is intended to by synonymous with "nucleic acid base or mimetic thereof" as herein described. In general, a nucleobase is any substructure that contains one or more atoms or groups of atoms capable of hydrogen bonding to a base of an oligonucleotide. Thus, the term "nucleobase" encompasses naturally-occurring purines and pyrimidines (guanine, adenine, thymine, cytidine and uracil), as well as protected analogs thereof and a wide variety of mimetic moieties as described herein.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine, 7-propynyl-7-deaza-8-azaguanine, 7-propynyl-7-deaza-8-azaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993.

Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethylribosyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

In general, the term base includes the term nucleobase as described above. The term "base" means a binding member, as described hereinabove. While nucleobases are generally heterocyclic moieties, the term "base" as used herein with means any moiety or residue capable of participating in specific binding to a naturally occurring nucleobase residue.

G-clamps, Cytidine Analogs and Phenoxazines

In some embodiments of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications selectively bind to guanosines. Hence they have been termed G-clamps or cytidine analogs. Many of these polycyclic heterocyclic compounds have the general formula:

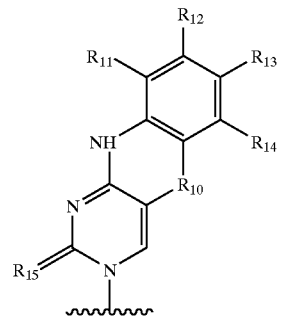

Representative cytosine analogs that make 3 hydrogen bonds with a guanosine in a second strand include 1,3-diazaphenoxazine-2-one ($R_{10}$=O, $R_{11}$–$R_{14}$=H) [Kurchavov, et al., *Nucleosides and Nucleotides*, 1997, 16, 1837–1846], 1,3-diazaphenothiazine-2-one ($R_{10}$=S, $R_{11}$–$R_{14}$=H), [Lin, K.-Y.; Jones, R. J.; Matteucci, M. J. Am. Chem. Soc. 1995, 117, 3873–3874] and 6,7,8,9-tetrafluoro-1,3-diazaphenoxazine-2-one ($R_{10}$=O, $R_{11}$–$R_{14}$=F) [Wang, J.; Lin, K.-Y., Matteucci, M. Tetrahedron Lett. 1998, 39, 8385–8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. patent application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—($CH_2$)$_2$—$NH_2$, $R_{12\text{-}14}$=H) [Lin, K.-Y.; Matteucci, M. J. Am. Chem. Soc. 1998, 120, 8531–8532]. Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety. Such compounds include those having the formula:

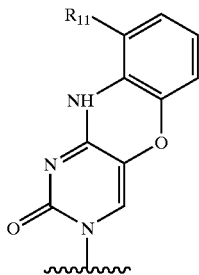

wherein $R_{11}$ includes $(CH_3)_2N—(CH_2)_2—O—$; $H_2N—(CH_2)_3—$; $Ph-CH_2—O—C(=O)—N(H)—(CH_2)_3—$; $H_2N—$; Fluorenyl-$CH_2—O—C(=O)—N(H)—(CH_2)_3—$; Phthalimidyl-$CH_2—O—C(=O)—N(H)—(CH_2)_3—$; Ph-$CH_2—O—C(=O)—N(H)—(CH_2)_2—O—$; Ph-$CH_2—O—C(=O)—N(H)—(CH_2)_3—O—$; $(CH_3)_2N—N(H)—(CH_2)_2—O—$; Fluorenyl-$CH_2—O—C(=O)—N(H)—(CH_2)_2—O—$; Fluorenyl-$CH_2—O—C(=O)—N(H)—(CH_2)_3—O—$; $H_2N—(CH_2)_2—O—CH_2—$; $N_3—(CH_2)_2—O—CH_2—$; $H_2N—(CH_2)_2—O—$, and $NH_2C(=NH)NH—$.

Also disclosed are tricyclic heterocyclic compounds of the formula:

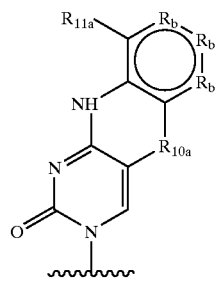

wherein
$R_{10a}$ is O, S or N—$CH_3$; $R_{11a}$ is $A(Z)_{x1}$, wherein A is a spacer and Z independently is a label bonding group bonding group optionally bonded to a detectable label, but $R_{11a}$ is not amine, protected amine, nitro or cyano; X1 is 1, 2 or 3; and
$R_b$ is independently —CH=, —N=, —C($C_{1-8}$ alkyl)= or —C(halogen)=, but no adjacent $R_b$ are both —N=, or two adjacent $R_b$ are taken together to form a ring having the structure:

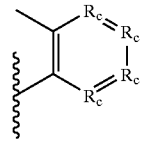

where $R_c$ is independently —CH=, —N=, —C($C_{1-8}$ alkyl)= or —C(halogen)=, but no adjacent $R_b$ are both —N=.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K.-Y.; Matteucci, M. J. Am. Chem. Soc. 1998, 120, 8531–8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513–3518]. Nevertheless, to optimize oligonucleotide design and to better understand the impact of these heterocyclic modifications on the biological activity, it is important to evaluate their effect on the nuclease stability of the oligomers.

Further tricyclic and tetracyclic heteroaryl compounds amenable to the present invention include those having the formulas:

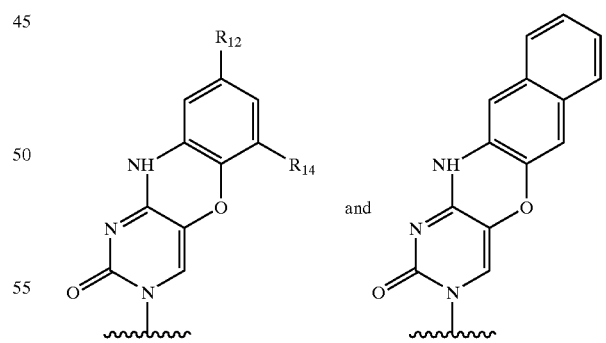

wherein $R_{14}$ is $NO_2$ or both $R_{14}$ and $R_{12}$ are independently —$CH_3$. The synthesis of these compounds is disclosed in U.S. Pat. No. 5,434,257, which issued on Jul. 18, 1995, U.S. Pat. No. 5,502,177, which issued on Mar. 26, 1996, and U.S. Pat. No. 5,646,269, which issued on Jul. 8, 1997, the contents of which are commonly assigned with this application and are incorporated herein in their entirety.

Further tricyclic heterocyclic compounds amenable to the present invention also disclosed in the "257, 177 and 269" patents include those having the formula:

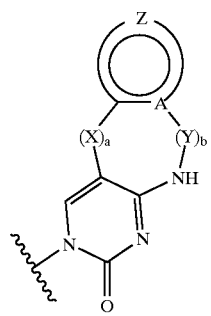

a and b are independently 0 or 1 with the total of a and b being 0 or 1;

A is N, C or CH;

X is S, O, C=O, NH or NCH$_2$, R$^6$;

Y is C=O;

Z is taken together with A to form an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a C atom, 2 N ring heteroatoms separated by a carbon atom, or 3 N ring heteroatoms at least 2 of which are separated by a carbon atom, and wherein the aryl or heteroaryl ring carbon atoms are unsubstituted with other than H or at least 1 non-bridging ring carbon atom is substituted with R$^{20}$ or =O;

or Z is taken together with A to form an aryl ring structure comprising 6 ring atoms wherein the aryl ring carbon atoms are unsubstituted with other than H or at least 1 non-bridging ring carbon atom is substituted with R$^6$ or =O;

R$^6$ is independently H, C$_{1-6}$ alkyl, C$_{2-6}$ alkenyl, C$_{2-6}$ alkynyl, NO$_2$, N(R$^3$)$_2$, CN or halo, or an R$^6$ is taken together with an adjacent Z group R$^6$ to complete a phenyl ring;

R$^{20}$ is, independently, H, C$_{1-6}$ alkyl, C$_{2-6}$ alkyl, C$_{2-6}$ alkenyl, C$_{2-6}$ alkynyl, NO$_2$, N(R$^{21}$)$_2$, CN, or halo, or an R$^{20}$ is taken together with an adjacent R$^{20}$ to complete a ring containing 5 or 6 ring atoms, and tautomers, solvates and salts thereof;

R$^{21}$ is, independently, H or a protecting group;

R$^3$ is a protecting group or H; and tautomers, solvates and salts thereof.

More specific examples included in the "257, 177 and 269" patents are compounds of the formula:

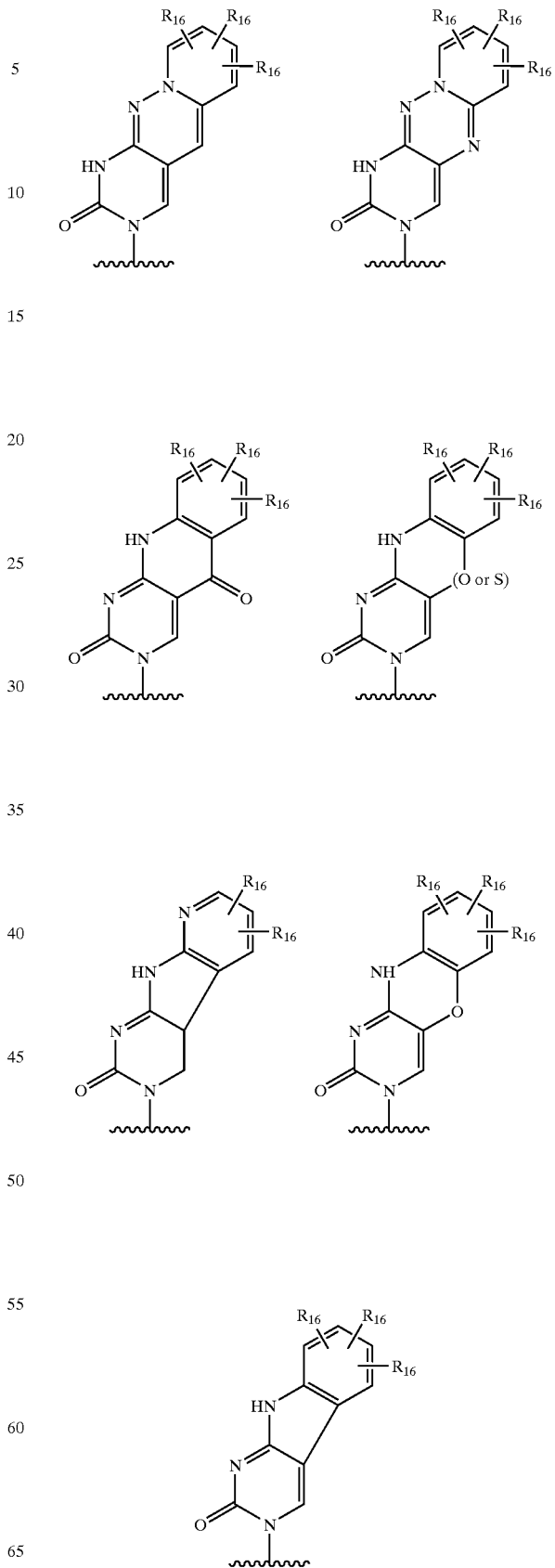

-continued

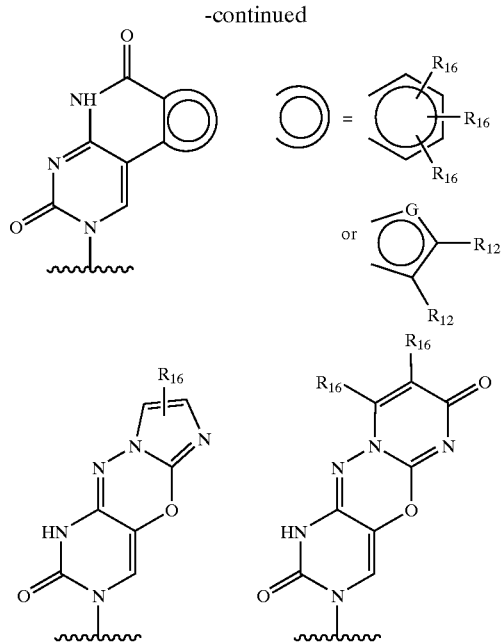

wherein each $R_{16}$, is, independently, selected from hydrogen and various substituent groups.

Further polycyclic base moieties having the formula:

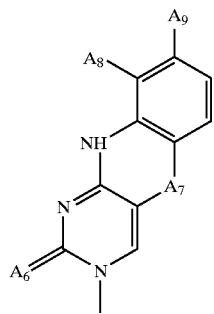

wherein:
$A_6$ is O or S;
$A_7$ is $CH_2$, N—$CH_3$, O or S;
each $A_8$ and $A_9$ is hydrogen or one of $A_8$ and $A_9$ is hydrogen and the other of $A_8$ and $A_9$ is selected from the group consisting of:
—O—$(CH_2)_{p1}$—G and

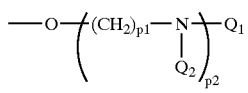

wherein:
G is —CN, —$OA_{10}$, —$SA_{10}$, —N(H)$A_{10}$, —ON(H)$A_{10}$ or —C(=NH)N(H)$A_{10}$;
$Q_1$ is H, —$NHA_{10}$, —C(=O)N(H)$A_{10}$, —C(=S)N(H)$A_{10}$ or —C(=NH)N(H)$A_{10}$;
each $Q_2$ is, independently, H or Pg;
$A_{10}$ is H, Pg, substituted or unsubstituted $C_1$–$C_{10}$ alkyl, acetyl, benzyl, —$(CH_2)_{p3}NH_2$, —$(CH_2)_{p3}N(H)Pg$, a D or L α-amino acid, or a peptide derived from D, L or racemic α-amino acids;
Pg is a nitrogen, oxygen or thiol protecting group;
each p1 is, independently, from 2 to about 6;
p2 is from 1 to about 3; and
p3 is from 1 to about 4;
are disclosed in U.S. patent application Ser. No. 09/996,292 filed Nov. 28, 2001, which is commonly owned with the instant application, and is herein incorporated by reference.

While the present invention is concerned primarily with oligonucleotides, some oligonucleotide mimetics may, with appropriate changes to the starting materials, also be prepared by processes according to the present invention. Oligonucleotide mimetics include compounds in which the oligonucleotide sugar has been replaced with a heterocyclic or carbocyclic ring structure. Such compounds are depicted in Formula 3, below.

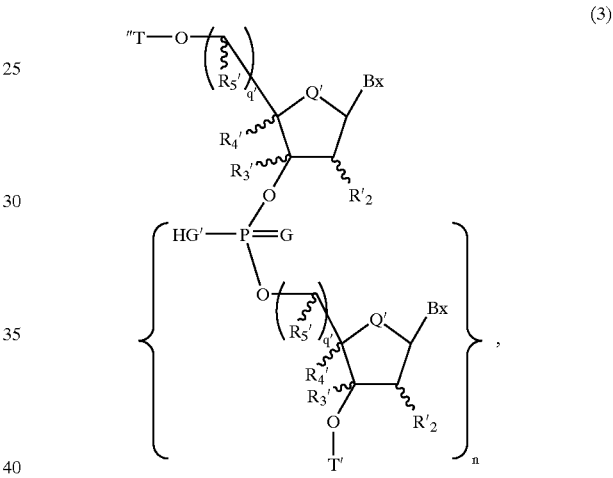

(3)

and tautomers, salts and solvates thereof.

In Formula 3, G, G', Bx, n, $R_2'$ and $R_4'$ each have the meanings previously defined. In addition, $R_{5'}$ may form, together with $R_{4'}$, a ring structure, which optionally includes another ring and $R_3$ is H or a substituent group. The groups T' and T'' are each H, or conjugate groups, such as protecting groups and substituents. Each Q' is independently O, S, NR''', C(R''')$_2$, or —CR'''=CR'''—, where each R''' is H, alkyl, or where two R''' groups are on the same or adjacent carbon atoms, they may form a carbocyclic or heterocyclic ring, wherein the ring contains one or two of N, O or S. Preferred values of R''' are H and $C_1$–$C_4$ alkyl.

The foregoing oligonucleotides and oligonucleotide mimetics may be manufactured by any art-recognized method of forming phosphate diester or phosphorothioate diester linkages between successive nucleoside or nucleoside mimetic units. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

A preferred process of synthesizing oligomeric compounds utilizes phosphoramidite chemistry on a support media. The phosphoramidites can modified at the heterocyclic base, the sugar, or both positions to enable the synthesis of oligonucleotides and modified oligonucleotides.

Illustrative examples of the synthesis of particular modified oligonucleotides may be found in the following U.S. patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, issued Jun. 29, 1993, and U.S. Pat. No. 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides.

The phosphoramidite method is as follows:

Phosphoramidites are prepared by reacting a suitable nucleoside or modified nucleoside (formula 4) with a phosphorodiamidite (formula 5) to form a phosphoramidite (formula 6).

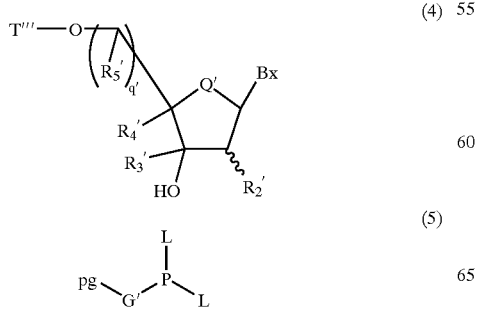

(4)

(5)

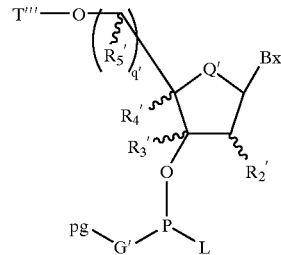

(6)

Each of the variables Q', Bx, $R_{2'}$, $R_{3'}$, $R_{4'}$, $R_{5'}$, G', and q' is as previously defined. L is an amine leaving group; pg is a phosphorus protecting group; and T''' is a hydroxyl protecting group, each as more specifically defined herein.

A support-bound nucleoside of Formula 7 is first deprotected at the 5'-position (resulting in a free 5'-OH group), after which a first amidite is coupled to a support-bound nucleoside to form a support-bound dimer of Formula 8, which is then oxidized, and subjected to a capping step to form a support bound dimer of Formula 9.

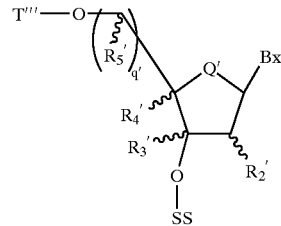

(7)

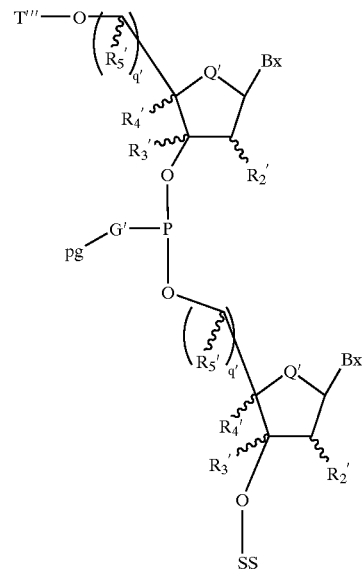

(8)

-continued

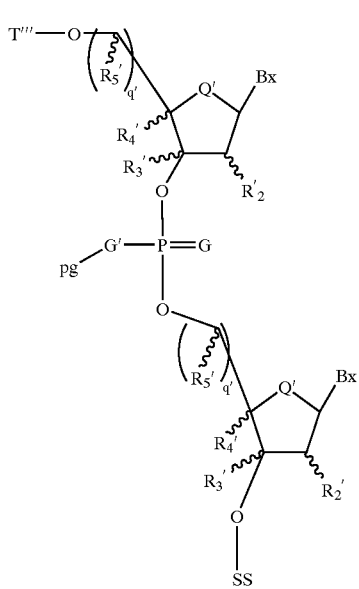
(9)

The 5'-deprotection, coupling, oxidation and capping steps are then repeated n-2 times to form a support-bound oligomer of Formula 10.

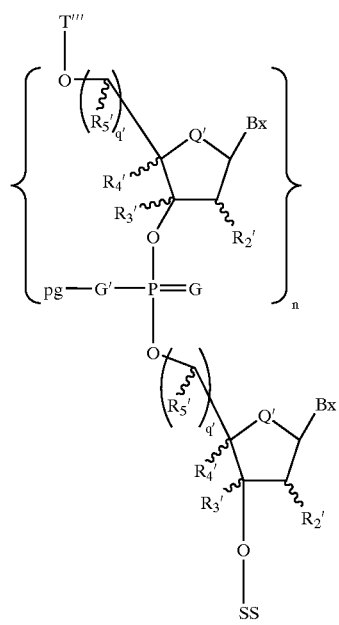
(10)

This compound is then cleaved from the solid support, 5'-deprotected, and purified to yield an oligomer of Formula (3), wherein T' is H. The oligonucleotide may then be further derivatized, purified, precipitated, or otherwise treated, as described in more detail herein.

In each of the foregoing Formulae, SS represents a support bound to the 3'-terminal nucleoside by a cleavable linker, each pg is a phosphorus protecting group as defined herein, n is an integer, G and G' are independently O or S, and each Bx, $R_{2'}$, $R_{3'}$, $R'_4$, $R_5'$, Q', and q' is independently as defined in Formula 3.

In addition to phosphate diester and phosphorothioate diester linkages, other linkers are known in the art. While the primary concern of the present invention has to do with phosphate diester and phosphorothioate diester oligonucleotides, chimeric compounds having more than one type of linkage, as well as oligomers having non-phosphate/phosphorothioate diester linkages as described in further detail below, are also contemplated in whole or in part within the context of the present invention.

Exemplary non-phosphate/phosphorothioate diester linkages contemplated within the skill of the art include: phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates. Additional linkages include: thiodiester (—O—C(O)—S—), thionocarbamate (—O—C(O)(NJ)—S—), siloxane (—O—Si(J)$_2$—O—), carbamate (—O—C(O)—NH— and —NH—C(O)—O—), sulfamate (—O—S(O)(O)—N— and —N—S(O)(O)—N—, morpholino sulfamide (—O—S(O)(N(morpholino)-), sulfonamide (—O—SO$_2$—NH—), sulfide (—CH$_2$—S—CH$_2$—), sulfonate (—O—SO$_2$—CH$_2$—), N,N'-dimethylhydrazine (—CH$_2$—N(CH$_3$)—N(CH$_3$)—), thioformacetyl (—S—CH$_2$—O—), formacetal (—O—CH$_2$—O—), thioketal (—S—C(J)$_2$—O—), ketal (—O—C(J)$_2$—O—), amine (—NH—CH$_2$—CH$_2$—), hydroxylamine (—CH$_2$—N(J)—O—), hydroxylimine (—CH=N—O—), and hydrazinyl (—CH$_2$—N(H)—N(H)—).

In each of the foregoing substructures relating to internucleoside linkages, J denotes a substituent group which is commonly hydrogen or an alkyl group or a more complicated group that varies from one type of linkage to another.

In addition to linking groups as described above that involve the modification or substitution of the —O—P—O— atoms of a naturally occurring linkage, included within the scope of the present invention are linking groups that include modification of the 5'-methylene group as well as one or more of the —O—P—O— atoms. Linkages of this type are well documented in the prior art and include without limitation the following: amides (—CH$_2$—CH$_2$—N(H)—C(O)) and —CH$_2$—O—N=CH—; and alkylphosphorus (—C(J)$_2$—P(=O)(OJ)—C(J)$_2$—C(J)$_2$—). J is as described above.

Synthetic schemes for the synthesis of the substitute internucleoside linkages described above are disclosed in: U.S. Pat. Nos. 5,466,677; 5,034,506; 5,124,047; 5,278,302; 5,321,131; 5,519,126; 4,469,863; 5,455,233; 5,214,134; 5,470,967; 5,434,257. Additional background information relating to internucleoside linkages can be found in: WO 91/08213; WO 90/15065; WO 91/15500; WO 92/20822; WO 92/20823; WO 91/15500; WO 89/12060; EP 216860; PCT/US 92/04294; PCT/US 90/03138; PCT/US 91/06855; PCT/US 92/03385; PCT/US 91/03680; U.S. application Ser. Nos. 07/990,848; 07/892,902; 07/806,710; 07/763,130; 07/690,786; Stirchak, E. P., et al., Nucleic Acid Res., 1989, 17, 6129–6141; Hewitt, J. M., et al., 1992, 11, 1661–1666; Sood, A., et al., J. Am. Chem. Soc., 1990, 112, 9000–9001; Vaseur, J. J. et al., J. Amer. Chem. Soc., 1992, 114, 4006–4007; Musichi, B., et al., J. Org. Chem., 1990, 55, 4231–4233; Reynolds, R. C., et al., J. Org. Chem., 1992, 57, 2983–2985; Mertes, M. P., et al., J. Med. Chem., 1969, 12, 154–157; Mungall, W. S., et al., J. Org. Chem., 1977, 42, 703–706; Stirchak, E. P., et al., J. Org. Chem., 1987, 52, 4202–4206; Coull, J. M., et al., Tet. Lett., 1987, 28, 745; and Wang, H., et al., Tet. Lett., 1991, 32, 7385–7388.

Phosphoramidites used in the synthesis of oligonucleotides are available from a variety of commercial sources (included are: Glen Research, Sterling, Va.; Amersham Pharmacia Biotech Inc., Piscataway, N.J.; Cruachem Inc., Aston, Pa.; Chemgenes Corporation, Waltham, Mass.; Proligo LLC, Boulder, Colo.; PE Biosystems, Foster City Calif.; Beckman Coulter Inc., Fullerton, Calif.). These commercial sources sell high purity phosphoramidites generally having a purity of better than 98%. Those not offering an across the board purity for all amidites sold will in most cases include an assay with each lot purchased giving at least the purity of the particular phosphoramidite purchased. Commercially available phosphoramidites are prepared for the most part for automated DNA synthesis and as such are prepared for immediate use for synthesizing desired sequences of oligonucleotides. Phosphoramidites may be prepared by methods disclosed by e.g. Caruthers et al. (U.S. Pat. Nos. 4,415,732; 4,458,066; 4,500,707; 4,668,777; 4,973,679; and 5,132,418) and Köster et al. (U.S. Pat. No. RE 34,069).

Oligonucleotides are generally prepared, as described above, on a support medium, e.g. a solid support medium. In general a first synthon (e.g. a monomer, such as a nucleoside) is first attached to a support medium, and the oligonucleotide is then synthesized by sequentially coupling monomers to the support-bound synthon. This iterative elongation eventually results in a final oligomeric compound or other polymer such as a polypeptide. Suitable support media can be soluble or insoluble, or may possess variable solubility in different solvents to allow the growing support bound polymer to be either in or out of solution as desired. Traditional support media such as solid supports are for the most part insoluble and are routinely placed in reaction vessels while reagents and solvents react with and/or wash the growing chain until the oligomer has reached the target length, after which it is cleaved from the support and, if necessary further worked up to produce the final polymeric compound. More recent approaches have introduced soluble supports including soluble polymer supports to allow precipitating and dissolving the iteratively synthesized product at desired points in the synthesis (Gravert et al., Chem. Rev., 1997, 97, 489–510).

The term support media (support) is intended to include all forms of support known to the art skilled for the synthesis of oligomeric compounds and related compounds such as peptides. Some representative support media that are amenable to the methods of the present invention include but are not limited to the following: controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, Angew. Chem. Internal. Ed. 1972, 11, 314, sold under the trademark "PORASIL E" by Waters Associates, Framingham, Mass., USA); the mono ester of 1,4-dihydroxymethylbenzene and silica (see Bayer and Jung, Tetrahedron Lett., 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support media, polyethylene glycol PEG's (see Bonora et al., Organic Process Research & Development, 2000, 4, 225–231).

Further support media amenable to the present invention include without limitation PEPS support a polyethylene (PE) film with pendant long-chain polystyrene (PS) grafts (molecular weight on the order of $10^6$, (see Berg, et al., J. Am. Chem. Soc., 1989, 111, 8024 and International Patent Application WO 90/02749),). The loading capacity of the film is as high as that of a beaded matrix with the additional flexibility to accommodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwell plates have not indicated any limitations of the synthetic efficacy.

Further support media amenable to the present invention include without limitation particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., J. Am. Chem. Soc., 1975, 97, 6584, Bioorg. Chem. 1979, 8, 351, and J. C. S. Perkin 1538 (1981)).

Further support media amenable to the present invention include without limitation a composite of a resin and another material that is also substantially inert to the organic synthesis reaction conditions employed. One exemplary composite (see Scott, et al., J. Chrom. Sci., 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, Israel J. Chem. 1978, 17, 243 and van Rietschoten in Peptides 1974, Y. Wolman, Ed., Wiley and Sons, New York, 1975, pp. 113–116). Contiguous solid supports other than PEPS, such as cotton sheets (Lebl and Eichler, Peptide Res. 1989, 2, 232) and hydroxypropylacrylate-coated polypropylene membranes (Daniels, et al., Tetrahedron Lett. 1989, 4345). Acrylic acid-grafted polyethylene-rods and 96-microtiter wells to immobilize the growing peptide chains and to perform the compartmentalized synthesis. (Geysen, et al., Proc. Natl. Acad. Sci. USA, 1984, 81, 3998). A "tea bag" containing traditionally-used polymer beads. (Houghten, Proc. Natl. Acad. Sci. USA, 1985, 82, 5131). Simultaneous use of two different supports with different densities (Tregear, Chemistry and Biology of Peptides, J. Meienhofer, ed., Ann Arbor Sci. Publ., Ann Arbor, 1972 pp. 175–178). Combining of reaction vessels via a manifold (Gorman, Anal. Biochem., 1984, 136, 397). Multicolumn solid-phase synthesis (e.g., Krchnak, et al., Int. J. Peptide Protein Res., 1989, 33, 209), and Holm and Meldal, in "Proceedings of the 20th European Peptide Symposium", G. Jung and E. Bayer, eds., Walter de Gruyter & Co., Berlin, 1989 pp. 208–210). Cellulose paper (Eichler, et al., *Collect. Czech. Chem. Commun.*, 1989, 54, 1746). Support mediated synthesis of peptides have also been reported (see, *Synthetic Peptides: A User's Guide*, Gregory A. Grant, Ed. Oxford University Press 1992; U.S. Pat. Nos. 4,415,732; 4,458,066; 4,500,707; 4,668,777; 4,973,679; 5,132,418; 4,725,677 and Re-34,069.)

Support bound oligonucleotide synthesis relies on sequential addition of nucleotides to one end of a growing chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Köster U.S. Pat. Nos. 4,725,677 and Re. 34,069.

Commercially available equipment routinely used for the support media based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

In general, the phosphorus protecting group (pg) is an alkyl group or a β-eliminable group having the formula —$CH_2CH_2$—$G_w$, wherein $G_w$ is an electron-withdrawing group. Suitable examples of pg that are amenable to use in connection with the present invention include those set forth in the Caruthers U.S. Pat. Nos. 4,415,732; 4,458,066; 4,500,707; 4,668,777; 4,973,679; and 5,132,418; and Köster U.S. Pat. Nos. 4,725,677 and Re. 34,069. In general the alkyl or cyanoethyl withdrawing groups are preferred, as commercially available phosphoramidites generally incorporate either the methyl or cyanoethyl phosphorus protecting group.

The method for removal of phosphorus protecting groups (pg's) depends upon the specific pg to be removed. The β-eliminable groups, such as those disclosed in the Köster et al. patents, are generally removed in a weak base solution, whereby an acidic β-hydrogen is extracted and the —$CH_2CH_2$—$G_w$ group is eliminated by rearrangement to form the corresponding acrylo-compound $CH_2$=CH—$G_w$. In contrast, an alkyl group is generally removed by nucleophilic attack on the α-carbon of the alkyl group. Such pg's are described in the Caruthers et al. patents, as cited herein.

The person skilled in the art will recognize that oxidation of P(III) to P(V) can be carried out by a variety of reagents. Furthermore, the person skilled in the art will recognize that the P(V) species can exist as phosphate triesters, phosphorothioate diesters, or phosphorodithioate diesters. Each type of P(V) linkage has uses and advantages, as described herein. Thus, the term "oxidizing agent" should be understood broadly as being any reagent capable of transforming a P(III) species (e.g. a phosphite) into a P(V) species. Thus the term "oxidizing agent" includes "sulfurizing agent," and oxidation will be understood to embrace both introduction of oxygen and introduction of sulfur, or sulfurization. Where it is important to indicate that an oxidizing agent introduces an oxygen into a P(III) species to make a P(V) species, the oxidizing agent will be referred to herein is "an oxygen-introducing oxidizing reagent."

Oxidizing reagents for making phosphate diester linkages (i.e. oxygen-introducing oxidizing reagents) under the phosphoramidite protocol have been described by e.g. Caruthers et al. and Köster et al., as cited herein. Examples of sulfurization reagents which have been used to synthesize oligonucleotides containing phosphorothioate bonds include elemental sulfur, dibenzoyltetrasulfide, 3-H-1,2-benzidithiol-3-one 1,1-dioxide (also known as Beaucage reagent), tetraethylthiuram disulfide (TETD), and bis(O,O-diisopropoxy phosphinothioyl)disulfide (known as Stec reagent). Oxidizing reagents for making phosphorothioate diester linkages include phenyl acetyl disulfide (PADS), as described by Cole et al. in U.S. Pat. No. 6,242,591. In some embodiments of the invention, the phosphorothioate diester and phosphate diester linkages may alternate between sugar subunits. In other embodiments of the present invention, phosphorothioate linkages alone may be employed.

Various solvents may be used in the oxidation reaction. Suitable solvents are identified in the Caruthers et al. and Köster et al. patents, cited herein. The Cole et al. patent describes acetonitrile as a solvent for phenyl acetyl disulfide. Other suitable solvents include toluene, xanthenes, dichloromethane, etc.

Reagents for cleaving an oligonucleotide from a support are set forth, for example, in the Caruthers et al. and Köster et al. patents, as cited herein.

Oligonucleotides as defined herein generally include salts, solvates and tautomers of oligonucleotides. In general, many bases, especially nucleobases, can form tautomeric structures that are included within the general definitions of oligonucleotides according to the present invention. In addition, the phosphorothioate linker can form the following tautomers:

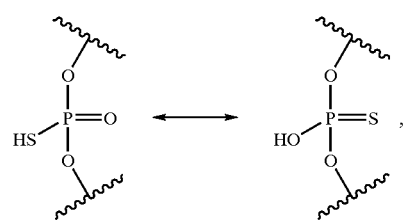

and can likewise form the following salt structures:

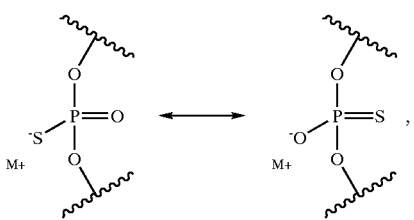

wherein M⁺ is a suitable salt-forming cation, such as $Na^+$, $K^+$, ½ $Ca^{2+}$, ½ $Mg^{2+}$, ⅓ $Al^{3+}$, $NH_4^+$, $H_3O^+$, etc. (The fractions indicate fractional equivalents of the cationic species per phosphate diester linkage.)

The oligonucleotide may be worked up by standard procedures known in the art, for example by size exclusion chromatography, high performance liquid chromatography (e.g. reverse-phase HPLC), differential precipitation, etc. In some embodiments according to the present invention, the oligonucleotide is cleaved from a solid support while the 5'-OH protecting group is still on the ultimate nucleoside. This so-called DMT-on (or trityl-on) oligonucleotide is then subjected to chromatography, after which the DMT group is removed by treatment in an organic acid, after which the oligonucleotide is de-salted and further purified to form a final product.

The 5'-hydroxyl protecting groups may be any groups that are selectively removed under suitable conditions. In particular, the 4,4'-dimethoxytriphenylmethyl (DMT) group is a favored group for protecting at the 5'-position, because it is readily cleaved under acidic conditions (e.g. in the presence of dichloroacetic acid (DCA), trichloroacetic acid (TCA), or acetic acid. Removal of DMT from the support-bound oligonucleotide is generally performed with DCA. Removal, of oligonucleotide after cleavage from the support is generally performed with acetic acid. Other 5'-protecting groups include the pixyl and thiopixyl groups, and derivatives thereof, as described herein.

As described herein, oligonucleotides can be prepared as chimeras with other oligomeric moieties. In the context of this invention, the term "oligomeric compound" refers to a polymeric structure capable of hybridizing a region of a nucleic acid molecule, and an "oligomeric moiety" a portion of such an oligomeric compound. Oligomeric compounds include oligonucleotides, oligonucleosides, oligonucleotide analogs, modified oligonucleotides and oligonucleotide mimetics. Oligomeric compounds can be linear or circular, and may include branching. They can be single stranded or double stranded, and when double stranded, may include overhangs. In general an oligomeric compound comprises a backbone of linked monomeric subunits where each linked monomeric subunit is directly or indirectly attached to a heterocyclic base moiety. The linkages joining the monomeric subunits, the monomeric subunits and the heterocyclic base moieties can be variable in structure giving rise to a plurality of motifs for the resulting oligomeric compounds including hemimers, gapmers and chimeras. As is known in the art, a nucleoside is a base-sugar combination. The base portion of the nucleoside is normally a heterocyclic base moiety. The two most common classes of such heterocyclic bases are purines and pyrimidines. In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In the context of this invention, the term "oligonucleotide mimetic" refers to an oligonucleotide wherein the backbone of the nucleotide units has been replaced with novel groups. Although the term is intended to include oligomeric compounds wherein only the furanose ring or both the furanose ring and the internucleotide linkage are replaced with novel groups, replacement of only the furanose ring is also referred to in the art as being a sugar surrogate. Oligonucleotide mimetics can be further modified to incorporate one or more modified heterocyclic base moieties to enhance properties such as hybridization.

EXAMPLES

The present invention may be further appreciated upon reference to the following, non-limiting examples.

Example 1

MOE T DMT (Using Lutidine as Base and Solvent)

2'-O-(2-Methoxyethyl)-5-methyluridine (MOE T, 16 g, 50.6 mmol) was dissolved in 2,6-lutidine (100 ml) and 4,4'-dimethoxytrityl chloride (DMTCl, 20.3 g, 60 mmol) was added. The mixture was stirred at room temperature for 30 min. and methanol (MeOH, 1 ml) was added. The mixture was concentrated under reduced pressure. The residue was dissolved in toluene (200 ml) and washed with aqueous sodium bicarbonate ($NaHCO_3$, 3×100 ml), dried (over $Na_2SO_4$) and evaporated to approximately 100 g. Hexane (150 ml) was added. The mixture was shaken for 5 min. and the supernatant was decanted. The residue was dried to give a yellow solid (30.1 g, 96%).

Example 2

MOE T DMT Purified (by Base Extraction)

In a 50 L glass-lined steel reactor, 2'-O-(2-methoxyethyl)-5-methyluridine (MOE T, 1500 g, 4.738 mol), lutidine (1015 g, 9.476 mol) were dissolved in anhydrous acetonitrile (15 L). The solution was stirred rapidly and chilled to −10° C. (all temperatures internal). Dimethoxytriphenylmethyl chloride (DMTCl, 1765.7 g, 5.21 mol) was added as a solid in one portion. The reaction was allowed to warm up to −2° C. over 1 h. The reaction was monitored closely by TLC (ethyl acetate) to judge when to stop the reaction, as the 3',5'-bis DMT first became noticeable after a heavy application (Rf just below DMTCl peak). At 60 min, TLC indicated a 85–90% complete reaction with no visible bis DMT spot. The reaction was allowed to warn from −2 to 3° C. over 25 min. The TLC now showed approximately 95% conversion, with a faint trace of the bis DMT impurity. The reaction was quenched by adding methanol (MeOH, 300 mL). After 10 min, the reaction was worked up by adding toluene (16 L) and then water (16 L). The solution was transferred to a clear 50 L vessel with a bottom outlet. After vigorous stirring for 1 minute, the layers separated easily. The aqueous layer was removed and the organic layer was washed successively with 10% aq. citric acid (8 L, no emulsion), and water (12 L, no emulsion). The organic layer volume at this point was 24 L, indicating that some acetonitrile was still present. The organic phase was extracted with aqueous sodium hydroxide (0.5 N, 16 L) to give two layers in about 10 min. The aqueous layer was a homogenous purplish-red solution which slowly faded to a light, reddish-brown color and the organic layer was a bright yellow color. TLC indicated a small amount of product remained in the organic layer so it was extracted with more base (8 L, 0.5 N). The second aqueous phase appeared more milky but this disappeared when mixed with the main aqueous layer (containing some acetonitrile co-solvent). The combined aqueous layer was overlaid with toluene (12 L). Solid citric acid (8 moles, 1270 g) was added with vigorous stirring. The pH of the aqueous layer was 5.5. The aqueous layer was drained and the organic layer was washed with water (10 L). TLC of the organic layer indicated a trace of DMT-O-Me, bis DMT and dimer DMT.

NOTE: A high load column (scrub column to remove baseline material) was used as follows to remove an impurity derived form an impurity in the starting nucleoside (a dimer of the nucleoside present at 0.5% concentration). If pure nucleoside was used as the starting material, the scrub column would be unnecessary.

In a 6 L sintered glass funnel, 4 L (approximately 2 Kg) of silica gel was slurried with toluene (2 L) and triethylamine (25 mL). The funnel was placed on a 20 L filter flask. The organic phase was slowly pumped on to the top of the funnel as suction was applied. Once complete, the funnel was washed with toluene (12 L) and then ethyl acetate (3×4 L individual fractions). A red colored DMT impurity band seemed to track with the dimer DMT. The fractions were concentrated on a rotary evaporator. TLC indicated that the first ethyl acetate fraction (220 g) contained a faint trace of dimer DMT and the second fraction (8.5 g) contained about 5% of the dimer and was discarded. The first ethyl acetate fraction was dissolved in toluene (2 L) and passed through silica gel as above (150 g) and washed with 2 L ethyl acetate. The clean fractions were combined with the main fraction in 2×20 L flasks and stripped to a foam and coevaporated with acetonitrile (3 L each) and dried (0.1 mm Hg, 40 h, 40° C.), until the weight loss was very slow, to give a white crisp foam, 2850 g. NMR showed a 0.25 mole % remainder of acetonitrile (calculates to ca. 47 g) to give a true dry weight of 2803 g (96%). HPLC showed a purity of 99.41 product (2'-O-(2-methoxyethyl)-5'-(4,4'-dimethoxytrityl)-5-methyluridine (MOE T DMT), 0.06 DMT-O-Me, 0.10 unknown, 0.44 bis DMT, and no detectable dimer DMT or 3'-O-DMT.

HPLC conditions C-18 in a gradient of acetonitrile-0.1 M TEAA buffer from 5% to 95% over 20 min. Then hold at 95% acetonitrile for 20 min.

HPLC relative retention times verified by co-injection with authentic samples:
  Dimer DMT 19.9 min.
  MOE-T-5'-DMT 21.2 min.
  MOE-T-3'-DMT 22.0 min.
  DMT-OH 22.5 min.
  DMT-O-Me 25.7 min.
  MOE-T 3',5'-bis DMT 27.4 min.

Example 3

MOE T DMT (Purification Method by a Separate Succinate Reaction)

Crude 5'-O-(4,4'-dimethoxytrityl)-2'-O-(2-methoxyethyl)-5-methyluridine as prepared in the procedure above before base extraction (MOE T DMT, 200 g, 0.323 mol), succinic anhydride (64.7 g, 0.646 mol), and 2,6-dimethylaminopyridine (2,6-lutidine, 19.7 g, 0.162 mol) were dissolved in anhydrous pyridine (1 L) and stirred at ambient temperature for 2 h. TLC indicated a complete reaction. The reaction was quenched by the addition of water (50 mL) and the solution was concentrated on a rotary evaporator to a thick oil. The oil was dissolved in a mixture of toluene (1.5 L), 20% aq. citric acid (1.5 L) and then shaken vigorously. An emulsion formed, which never completely separated (leading to some yield loss). The separated organic layer was extracted with water containing 1 molar equivalent of sodium hydroxide. The pH of the water layer was 11.5–12. Note: Higher pH levels lead to extraction of the bis DMT via the thymine ring. The separated aqueous layer was acidified with 20% aq. citric acid (500 mL), which caused a white gum to form. The gum was slowly dissolved in toluene-ethyl acetate (1:1, 1 L). The organic layer was stripped and coevaporated with acetonitrile (300 mL) and dried to a white foam (143 g). Yield loss due to emulsion noted earlier.

A 7 g sample was dissolved in dioxane (20 mL) and then treated with concentrated ammonium hydroxide (10 mL). The reaction was sealed and stirred at ambient temperature. TLC after 4 days still showed 10% of the succinate remained. Aqueous methylamine ($CH_3NH_2$, 5 mL, 40%) was added. TLC after 24 h showed only a trace of succinate remained. The solution was diluted with water (100 mL) and then extracted with toluene (100 mL). TLC indicated the remaining succinate was in the water layer. The toluene layer was stripped and dried to 5.0 g of a white foam. The HPLC of the product appeared to have no detectable DMT-X or bis DMT peaks and thus appeared to be nearly 100% pure. Note: It is possible to add the succinate sequentially in the same pot as the DMT reaction.

Example 4

MOE T DMT Succinate (via an in situ Succinate Reaction)

Triethylammonium 5'-O-(4,4'-dimethoxytrityl)-2'-O-(2-methoxyethyl)-5-methyluridine-3'-O-succinate: 2'-O-(2-methoxyethyl)-5-methyluridine (MOE T, 15.8 g, 50 mmol) was dissolved in 2,6-lutidine (23.3 ml) and acetonitrile (150 ml). 4,4'-Dimethoxytrityl chloride (DMTCl, 18.6 g, 55 mmol) was added. The mixture was stirred at room temperature for 30 min. and methanol (MeOH, 0.2 ml) was added. After 10 min., triethylamine (20 ml) and succinic anhydride (15 g) were added and the mixture was stirred overnight. The mixture was concentrated under reduced pressure. The residue was dissolved in dichloromethane (200 ml) and washed with triethylammonium phosphate (0.5 M, pH 7, 3×100 ml). The organic layer was dried ($Na_2SO_4$) and evaporated to approximately 100 ml. Hexane (150 ml) was added. The mixture was shaken for 5 min. and the supernatant was decanted. The residue was dried to give a yellow solid (36.8 g, 90%).

Example 5

MOE T DMT (Purification via an in situ Succinate Reaction and Subsequent Cleavage)

5'-O-Dimethoxytrityl-2'-O-methoxyethyl-thymidine: 2'-O-(2-methoxyethyl)-5-methyuridine (15.8 g, 50 mmol) was dissolved in 2,6-lutidine (23.3 ml) and acetonitrile (150 ml). 4,4'-Dimethoxytrityl chloride (DMTCl, 18.6 g, 55 mmol) was added. The mixture was stirred at room temperature for 30 min. and methanol (MeOH, 0.2 ml) was added. After 10 min., triethylamine (15 ml) and succinic anhydride (15 g) were added and the mixture was stirred overnight. The mixture was concentrated under reduced pressure. The residue was dissolved in dichloromethane (300 ml) and washed with water (3×100 ml). The organic layer was evaporated. The residue was partitioned between toluene (200 ml) and ethylene glycol-water (1:1, 200 ml). The two layers were separated and the lower layer was extracted with toluene (200 ml). Methylamine (40% in water, 50 ml) was added to the lower layer and the mixture was heated at 50° C. for 2 h. The mixture was extracted with toluene (200 ml) and washed with water (3×200 ml). Evaporation of the toluene solution gave the final product (MOE T DMT, 5'-O-Dimethoxytrityl-2'-O-methoxyethyl-thymidine) as a colorless solid (28.2 g, 91%).

Example 6

MOE-T DMT (Purified by Base Extraction)

In a 50 L glass-lined steel reactor, 2'-O-(2-methoxyethyl)-5-methyl-uridine (MOE-T, 2000 g, 6.317 mol), 2,6-lutidine (1352 g, 12.63 mol) were dissolved in anhydrous acetonitrile (20 L). The solution was stirred rapidly and chilled to −15° C. (all temperatures internal). Dimethoxytriphenylmethyl chloride (DMTCl, 2354 g, 6.95 mol) was added as a solid in one portion. The reaction was allowed to warm slowly up to −2° C. over 1 h and then held at −2° C. for 30 min. The reaction was monitored closely by TLC (ethyl acetate) to judge when to stop the reaction as the starting material was nearly consumed and the first trace of 3',5'-bis DMT became noticeable after a very heavy application (Rf just below DMTCl peak). The reaction was quenched by adding methanol (400 mL). After 10 min, the reaction was worked up by adding toluene (22 L) and then water (22 L). The solution was transferred to a clear 50 L vessel with a bottom outlet. After vigorous stirring for 1 minute, the layers were permitted to separate over 30 min. The aqueous layer was removed and the organic layer was washed successively with 10% aqueous citric acid (11 L, no emulsion), and water (16 L, no emulsion). The organic layer volume at this point was 30 L indicating that some acetonitrile was still present. The organic phase was extracted with aqueous sodium hydroxide (0.5 N, 22 L) to give two layers in about 10 min. The aqueous layer was a homogenous purplish-red solution which slowly faded to a light reddish brown color and the organic layer was a bright yellow color. TLC indicated a small amount of product remained in the organic layer so it was extracted with more base (8 L, 0.5 N). The second aqueous phase appeared more milky but this disappeared when mixed with the main aqueous layer (containing some acetonitrile co-solvent). The combined aqueous layer was overlaid with toluene (16 L). Solid citric acid (6.5 moles, 1365 g) was added with vigorous stirring. The pH of the aqueous layer was 5.5. The aqueous layer was drained and the organic layer was washed with water (10 L). TLC of the organic layer indicated a faint trace of DMT-O-Me, bis DMT and dimer DMT.

In a 6 L sintered glass funnel, 4 L (ca 2 kg) of silica gel was slurried with toluene (2 L) and triethylamine (25 mL). The funnel was placed on a 20 L filter flask. The organic phase was slowly pumped on to the top of the funnel as suction was applied. Once complete, the funnel was washed with toluene (12 L) and then ethyl acetate-hexanes (1:1, 8 L), then ethyl acetate (3×4 L individual fractions). A red colored DMT impurity band seemed to track with the dimer DMT. The clean fractions (up to the start of the straight ethyl acetate) were combined and concentrated on three 20 L rotary evaporators to a foam and coevaporated with acetonitrile (3 L each) and dried (0.1 mm Hg, 40 h, 40° C.) till the weight loss was very slow to give a white crisp foam, 3900 g (ca 100%). NMR showed the presence of 0.25 mole % remainder of acetonitrile to give a true yield of about 96%. The purity was similar to an earlier lot in which the HPLC showed a purity of 99.41 product, 0.06 DMT-O-Me, 0.10 unknown, 0.44 bis DMT, and no detectable dimer DMT or 3'-O-DMT.

HPLC relative retention times verified by co-injection with authentic samples:
Dimer DMT 19.9 min
MOE-T-5'-DMT 21.2 min
MOE-T-3'-DMT 22.0 min
DMT-OH 22.5 min
DMT-O-Me 25.7 min
MOE-T 3',5'-bis DMT 27.4 min All references cited herein are expressly incorporated herein by reference.

The person having skill in the art will recognize that further embodiments are possible within the general scope of the foregoing description and the attached drawings and claims, and it would be within the skill of such skilled person to practice the invention as generally described herein.

We claim:

1. A process comprising contacting a nucleoside with a hindered aryl amine activator and a protecting reagent to produce a regioselectively 5' mono-protected nucleoside.

2. The process of claim 1, wherein the hindered aryl amine activator has the formula:

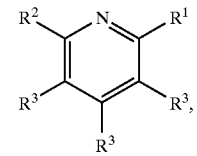

wherein each of $R^1$ and $R^2$ is H, alkyl or substituted alkyl, at least one of $R^1$ and $R^2$ being other than H, and each $R^3$ is independently H, alkyl or substituted alkyl, or two adjacent $R^3$ moieties are taken together to form a fused aromatic or aliphatic ring.

3. The process of claim 2, wherein $R^1$ is alkyl and $R^2$ is alkyl.

4. The process of claim 3, wherein $R^1$ is methyl or ethyl.

5. The process of claim 4, wherein $R^2$ is methyl or ethyl.

6. The process of claim 5, wherein $R^1$ is methyl and $R^2$ is methyl.

7. The process of claim 3, wherein each $R^3$ is H.

8. The process of claim 2, wherein $R^1$ is alkyl, $R^2$ is H, and $R^3$ is alkyl or substituted alkyl.

9. The process of claim 2, wherein $R^1$ is $C_3$–$C_6$ alkyl, $R^2$ is H and $R^3$ is H.

10. The process of claim 2, wherein two adjacent $R^3$ moieties are taken together to form a fused aromatic ring.

11. The process of claim 10, wherein the fused aromatic ring is a pyrido ring.

12. The process of claim 2, wherein two adjacent $R^3$ moieties are taken together to form an aliphatic ring.

13. The process of claim 2, wherein the hindered aryl amine activator is 2,6-dimethylpyridine.

14. The process of claim 1, wherein the nucleoside has the formula:

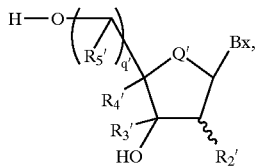

wherein $B_x$ is a nucleobase; $R_{2'}$ is H, OH, reversibly protected OH, a 2'-substitutent, or together with $R_{4'}$ forms a bridge; $R_{3'}$ is H or a substituent; $R_{4'}$ is H, alkyl, substituted alkyl, or together with $R_{2'}$ or $R_{5'}$ forms a bridge; $R_{5'}$ is H or together with $R_{4'}$ forms a bridge; Q' is O, S, NH, N-alkyl or $CH_2$; and q' is 0 or 1.

15. The process of claim 14, wherein the nucleoside has the formula:

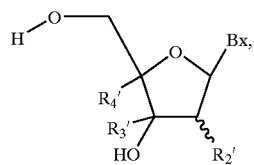

wherein $R_{2'}$ is H, OH, reversibly protected OH, a 2'-substituent, or together with $R_{4'}$ forms a bridge; $R_{3'}$ is H or a substituent; $R_{4'}$ is H, alkyl, substituted alkyl, or together with $R_{2'}$ forms a bridge.

16. The process of claim 15, wherein $R_{2'}$ is H or a substituent, or together with $R_{4'}$ forms a bridge; $R_{3'}$ is H, $R_{4'}$ is H or together with $R_{2'}$ forms a bridge.

17. The process of claim 16, wherein $R_{2'}$ is H or a substituent and $R_{4'}$ is H.

18. The process of claim 17, wherein $R_{2'}$ is H, methoxy or methoxyethoxy.

19. The process of claim 15, wherein the nucleoside has the formula:

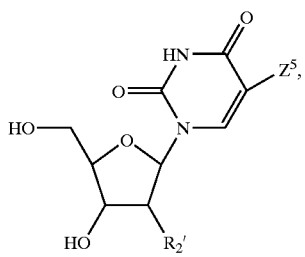

wherein $R_{2'}$ is H, OH, protected OH or a 2'-substituent; and
$Z^5$ is H or a ring substituent.

20. The process of claim 19, wherein $R_{2'}$ is H, OH, protected OH, $OCH_3$ or $OCH_2CH_2OCH_3$; and
$Z^5$ is alkyl or alkynyl.

21. The process of claim 19, wherein $R_{2'}$ is H, $OCH_3$ or $OCH_2CH_2OCH_3$.

22. The process of claim 19, wherein $Z^5$ is methyl or propynyl.

23. The process of claim 1, wherein the protected nucleoside has the formula:

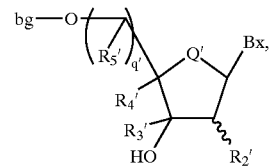

wherein $B_x$ is a nucleobase; $R_{2'}$ is H, OH, reversibly protected OH, a 2'-substitutent, or together with $R_{4'}$ forms a bridge; $R_{3'}$ is H or a substituent; $R_{4'}$ is H, alkyl, substituted alkyl, or together with $R_{2'}$ or $R_{5'}$ forms a bridge; $R_{5'}$ is H or together with $R_{4'}$ forms a bridge; Q' is O, S, NH, N-alkyl, $CH_2$; q' is 0 or 1, and bg is a protecting group.

24. The process of claim 23, wherein the protected nucleoside has the formula:

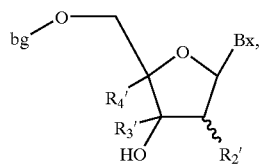

wherein $R_{2'}$ is H, OH, reversibly protected OH, a 2'-substitutent, or together with $R_{4'}$ forms a bridge; $R_{3'}$ is H or a substituent; $R_{4'}$ is H, alkyl, substituted alkyl, or together with $R_{2'}$ forms a bridge, and bg is a protecting group.

25. The process of claim 24, wherein bg is an optionally substituted trityl group, an optionally substituted pixyl group, or an optionally substituted thiopixyl group.

26. The process of claim 25, wherein bg is a substituted trityl group selected from 4-methoxytrityl and 4,4'-dimethoxytrityl.

27. The process of claim 26, wherein bg is 4,4'-dimethoxytrityl.

28. The process of claim 24, wherein the protected nucleoside is of the formula:

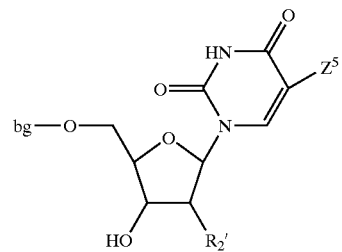

wherein bg is a 5'-protecting group;
$R_{2'}$ is H, OH, protected OH or a 2'-substituent; and
$Z^5$ is H, a ring substituent, or together with $Z^5$ form a ring, which may optionally be fused to one or more additional rings, and which optionally may be further substituted, or a tautomeric equivalent thereof.

29. The process of claim 28, wherein $R_{2'}$ is H, OH, protected OH, $OCH_3$ or $OCH_2CH_2OCH_3$; and
$Z^5$ is alkyl or alkynyl.

30. The process of claim 29, wherein $R_{2'}$ is H, $OCH_3$ or $OCH_2CH_2OCH_3$.

31. The process of claim 30, wherein $Z^5$ is methyl or propynyl.

32. The process of claim 31, wherein bg is 4,4'-dimethoxytrityl.

33. The process of claim 28, wherein $B_x$ is 5-methyluracil.

34. The process of claim 28, further comprising the steps of:
   (a) adding to the protected nucleoside a water-immiscible organic solvent to form a first organic phase;
   (b) contacting the first organic phase with a basic aqueous phase, whereby the protected nucleoside partitions into the basic aqueous phase;
   (c) acidifying the basic aqueous phase to form an acidic aqueous phase; and
   (d) extracting the nucleoside into a second organic phase.

35. The process of claim 34, wherein the basic aqueous phase has a pH in the range of about 8 to about 16.

36. The process of claim 34, wherein the acidic aqueous phase has a pH in the range of about 4.5 to about 6.8.

37. The process of claim 34, wherein the first organic phase comprises toluene.

38. The process of claim 28, further comprising reacting the protected nucleoside with a phosphitylating reagent to form a nucleoside phosphoramidite.

39. The process of claim 38, wherein the phosphitylating agent is a phosphorodiamidite.

40. The process of claim 1, wherein the protecting reagent is selected from an optionally substituted triphenylmethyl halide, an optionally substituted pixyl halide or an optionally substituted thiopixyl halide.

41. The process of claim 1, wherein the protecting reagent is 4,4'-dimethoxytrityl halide.

42. The process of claim 41, wherein the protecting reagent is 4,4'-dimethoxytrityl chloride.

43. The process of claim 1, further comprising steps for purifying the protected nucleoside.

44. The process of claim 43, wherein said steps for purifying the protected nucleoside comprise the steps of:
   providing the protected nucleoside in a first organic phase;
   contacting the first organic phase with an aqueous solution;
   extracting the protected nucleoside from the organic phase into a basic aqueous solution;
   adding acid to the basic aqueous solution to adjust the pH to a range of about 4.5 to about 6.8 to form an acidic aqueous solution; and
   extracting the protected nucleoside into an organic solvent to form a second organic phase, whereby a purified protected nucleoside is produced in the second organic phase.

45. The process of claim 44, wherein the first organic phase comprises a water-immiscible organic solvent.

46. The process of claim 45, wherein the water-immiscible organic solvent is toluene or ethyl acetate.

47. The process of claim 44, wherein the acid is citric acid.

48. The process of claim 44, further comprising reacting the purified protected nucleoside with a phosphitylating reagent to produce a phosphoramidite.

49. The process of claim 43, wherein said steps for purifying the protected nucleoside comprise:
   reacting the protected nucleoside with a derivatizing reagent to form a derivatized protected nucleoside;
   providing the derivatized protected nucleoside in a first organic phase;
   contacting the first organic phase with a basic aqueous phase, whereby the derivatized protected nucleoside partitions into the basic aqueous phase;
   acidifying the basic aqueous phase to form an acidic aqueous phase; and
   extracting the derivatized protected nucleoside into a second organic phase, whereby a purified derivatized protected nucleoside partitions into the second organic phase.

50. The process of claim 49, wherein the derivatizing reagent is represented by the formula:
   $X^L$-$L^N$-fg, wherein $X^L$ is a leaving group, $L^N$ is a linking group and fg is a functional group.

51. The process of claim 50, wherein $X^L$ is a halide, an alkylcarbonyloxy, or hydroxy, $L^N$ is CO-alkylene-, and fg is COOH, or $X^L$ and fg together form an anhydride.

52. The process of claim 49, wherein the derivatizing reagent is a member selected from the group consisting of diacids and diacid anhydrides.

53. The process of claim 52, wherein the derivatizing reagent is a diacid.

54. The process of claim 53, wherein the derivatizing reagent is succinic acid.

55. The process of claim 49, wherein the aqueous phase contains about 0.95 to about 1.05 molar equivalents of base per molar equivalent of derivatized protected nucleoside.

56. The process of claim 55, wherein the base is sodium hydroxide or potassium hydroxide.

57. The process of claim 49, further comprising reacting the derivatized protected nucleoside with a nucleophilic base to produce a purified protected nucleoside.

58. The process of claim 57, wherein the nucleophilic base comprises ammonium hydroxide or methylamine.

59. The process of claim 57, further comprising reacting the purified protected nucleoside with a phosphitylating reagent to produce a phosphoramidite.

60. The process of claim 49, further comprising reacting the derivatized protected nucleoside with a nucleoside support to form a primer support.

61. The process of claim 60, wherein the support is controlled pore glass or a polymer support.

62. The process of claim 49, further comprising removing the organic solvent from the protected nucleoside.

* * * * *